United States Patent
Deng et al.

(10) Patent No.: US 10,882,863 B2
(45) Date of Patent: Jan. 5, 2021

(54) COMPOUNDS FOR REDUCING C-MYC IN C-MYC OVEREXPRESSING CANCERS BACKGROUND

(71) Applicant: The Trustees of Columbia University in the City of New York, New York, NY (US)

(72) Inventors: Changchun Deng, Jericho, NY (US); Mark Lipstein, New York, NY (US); Owen O'Connor, Scarsdale, NY (US); Donald W. Landry, New York, NY (US); Xiaoming Xu, Fair Lawn, NJ (US); Shi-Xian Deng, White Plains, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 0 days.

(21) Appl. No.: 16/301,352

(22) PCT Filed: May 15, 2017

(86) PCT No.: PCT/US2017/032739
§ 371 (c)(1),
(2) Date: Nov. 13, 2018

(87) PCT Pub. No.: WO2018/013213
PCT Pub. Date: Jan. 18, 2018

(65) Prior Publication Data
US 2019/0194212 A1 Jun. 27, 2019

Related U.S. Application Data

(60) Provisional application No. 62/336,224, filed on May 13, 2016.

(51) Int. Cl.
| C07D 487/04 | (2006.01) |
| C07D 471/04 | (2006.01) |
| C07D 473/34 | (2006.01) |
| A61K 31/519 | (2006.01) |
| A61K 31/5377 | (2006.01) |
| A61K 45/06 | (2006.01) |
| G01N 33/574 | (2006.01) |
| A61P 35/00 | (2006.01) |

(52) U.S. Cl.
CPC .......... *C07D 487/04* (2013.01); *A61K 31/519* (2013.01); *A61K 31/5377* (2013.01); *A61K 45/06* (2013.01); *A61P 35/00* (2018.01); *C07D 471/04* (2013.01); *C07D 473/34* (2013.01); *G01N 33/57492* (2013.01); *G01N 2800/52* (2013.01)

(58) Field of Classification Search
CPC .................................................. C07D 487/04
See application file for complete search history.

(56) References Cited

FOREIGN PATENT DOCUMENTS

| CN | 104710297 A | 6/2015 |
| EP | 0004000 B1 | 11/1984 |
| WO | 2015001491 A1 | 1/2015 |

OTHER PUBLICATIONS

Pinedo et al. (2000).*
McMahon et al. (2000).*
Vippagunta et al. (2001).*
Chisholm, K.M., et al., Expression profiles of MYC protein and MYC gene rearrangement in lymphomas, Am J Surg Pathol, 2015, pp. 294-303; vol. 39(3).
Green, T.M., et al., Immunohistochemical double-hit score is a strong predictor of outcome in patients with diffuse large B-cell lymphoma treated with rituximab plus cyclophosphamide, doxorubicin, vincristine, and prednisone, J Clin Oncol, 2012, pp. 3460-3467; vol. 30(28).
Fingar, D.C., et al., Mammalian cell size is controlled by mTOR and its downstream targets S6K1 and 4EBP1/eIF4E, Genes Dev, 2002, pp. 1472-1487; vol. 16(12).
Hutter, G., et al., Proteasome inhibition leads to dephosphorylation and downregulation of protein expression of members of the Akt/mTOR pathway in MCL, Leukemia, 2012, pp. 2442-2444; vol. 26(11).
Tang, B., et al., Proteasome Inhibitors Activate Autophagy Involving Inhibition of PI3K-Akt- mTOR Pathway as an Anti-Oxidation Defense in Human RPE Cells, PLoS One, 2014, pp. e103364; vol. 9(7).
Pourdehnad, M., et al., Myc and mTOR converge on a common node in protein synthesis control that confers synthetic lethality in Myc-driven cancers. Proc Natl Acad Sci U S A, 2013, pp. 11988-11993; vol. 110(29).
Deng, C., et al., The novel IKK2 inhibitor LY2409881 potently synergizes with histone deacetylase inhibitors in preclinical models of lymphoma through the downregulation of NF-kappaB, Clin Cancer Res, 2015, pp. 134-145; vol. 21(1).
Herman, S.E., et al., Phosphatidylinositol 3-kinase-delta inhibitor CAL-101 shows promising preclinical activity in chronic lymphocytic leukemia by antagonizing intrinsic and extrinsic cellular survival signals, Blood, 2010, pp. 2078-2088; vol. 116(12).

(Continued)

*Primary Examiner* — Paul V Ward
(74) *Attorney, Agent, or Firm* — Wolter Van Dyke Davis, PLLC; Timothy H. Van Dyke

(57) ABSTRACT

The invention relates to new compounds that reduce c-Myc expression and useful for cancer treatment, particularly hematological cancers such as aggressive B- and T-cell lymphomas. The new compounds may be combined with adjunct c-Myc inhibor agents such as a PI3K inhibitor, CK-1 inhibitor, Akt-inhibitor, proteasome inhibitor and/or mTor inhibitor. The c-Myc reducing agent may be provided as a lead-in treatment to reduce or initiate reduction of c-Myc prior to administration of the adjunct cancer therapeutic agent. Treatment with a c-Myc reducing agent modulates the disease state of the c-Myc overexpressing cancer making it less malignant and more susceptible to adjunctive cancer therapies.

19 Claims, 5 Drawing Sheets

(56) References Cited

OTHER PUBLICATIONS

Lannutti, B.J., et al., CAL-101, a p110delta selective phosphatidylinositol-3-kinase inhibitor for the treatment of B-cell malignancies, inhibits PI3K signaling and cellular viability, Blood, 2011, pp. 591-594; vol. 117(2).

Gopal, A.K., et al., PI3Kdelta inhibition by idelalisib in patients with relapsed indolent lymphoma, The New England journal of medicine, 2014, pp. 1008-1018; vol. 370(11).

Furman, R.R., et al., Idelalisib and Rituximab in Relapsed Chronic Lymphocytic Leukemia, N Engl J Med, 2014, pp. 997-1007, vol. 370.

Burris, H.A., et al., TGR-1202, a Novel Once Daily PI3Kδ Inhibitor, Demonstrates Clinical Activity with a Favorable Safety Profile, Lacking Hepatotoxicity, in Patients with Chronic Lymphocytic Leukemia and B-Cell Lymphoma, Blood, 2014, pp. 1984-1984.

Mertz, J.A., et al., Targeting MYC dependence in cancer by inhibiting BET bromodomains, Proc Natl Acad Sci U S A, 2011, pp. 16669-16674; vol. 108(40).

Delmore, J.E., et al., BET bromodomain inhibition as a therapeutic strategy to target c-Myc, Cell, 2011, pp. 904-917; vol. 146(6).

Bordeleau, M.E., et al., Therapeutic suppression of translation initiation modulates chemosensitivity in a mouse lymphoma model, J Clin Invest, 2008, pp. 2651-2660; vol. 118(7).

Cencic, R., et al., Reversing chemoresistance by small molecule inhibition of the translation initiation complex eIF4F, Proc Natl Acad Sci U S A, 2011, pp. 1046-1051; vol. 108(3).

Moerke, N.J., et al., Small-molecule inhibition of the interaction between the translation initiation factors eIF4E and eIF4G, Cell, 2007, pp. 257-267; vol. 128(2).

Boussemart, L., et al., eIF4F is a nexus of resistance to anti-BRAF and anti-MEK cancer therapies, Nature, 2014, pp. 105-109, vol. 513.

Low, W.K., et al., Second-generation derivatives of the eukaryotic translation initiation inhibitor pateamine A targeting eIF4A as potential anticancer agents, Bioorg Med Chem, 2014, pp. 116-125; vol. 22(1).

Hutter, G., et al., The proteasome inhibitor bortezomib targets cell cycle and apoptosis and acts synergistically in a sequence-dependent way with chemotherapeutic agents in mantle cell lymphoma, Ann Hematol, 2012, pp. 847-856; vol. 91(6).

Cegielska, A., et al., Autoinhibition of casein kinase I epsilon (CKI epsilon) is relieved by protein phosphatases and limited proteolysis, J Biol Chem, 1998, pp. 1357-1364; vol. 273.

O'Connor, O.A., et al., A phase 1 dose escalation study of the safety and pharmacokinetics of the novel proteasome inhibitor carfilizomib (PR-171) in patients with hematologic malignancies, Clinical cancer research : an official journal of the American Association for Cancer Research, 2009, pp. 7085-7091; vol. 15(22).

Cheong, J.K., et al., IC261 induces cell cycle arrest and apoptosis of human cancer cells via CK1delta/varepsilon and Wnt/beta-catenin independent inhibition of mitotic spindle formation, Oncogene, 2011, pp. 2558-2569; vol. 30.

Rivers, A., et al., Regulation of casein kinase I epsilon and casein kinase I delta by an in vivo futile phosphorylation cycle, J Biol Chem, 1998, pp. 15980-15984; vol. 273.

Deng, C., et al, The PI3K Delta Inhibitor TGR-1202 and Proteasome Inhibitor Cartilzomib Are Highly Synergistic in Killing Human B- and T-Cell Lymphoma Cells, Blood, 2013, pp. 4421; vol. 122.

Long, A.M., et al., Structural basis for the potent and selective inhibition of casein kinase 1 epsilon, J Med Chem, 2012, pp. 10307-10311; vol. 55.

PUBCHEM-CID 102084273 Create Date: Dec. 24, 2015, pp. 1-8.
PUBCHEM-CID 90132482 Create Date: Feb. 13, 2015, pp. 1-11.
International Search Report and Written Opinion dated Sep. 27, 2017 in international application No. US17/32739, pp. 1-80.

\* cited by examiner

All drugs given at 25 μM

| Compound ID | Compound IC50* (M) CK1epsilon | Compound IC50* (µM) CK1epsilon |
|---|---|---|
| CUX-0404A | 3.21E-06 | 3.21 |
| TGR-1202 | 6.18E-07 | 0.62 |
| D4476* | 2.62E-07 | 0.26 |

COMPOUNDS FOR REDUCING C-MYC IN C-MYC OVEREXPRESSING CANCERS

BACKGROUND

CROSS-REFERENCE TO RELATED APPLICATIONS

This application is a 371 national stage application of PCT Application No. PCT/US17/32739 filed May 15, 2017 which claims benefit of Provisional Appln. 62/336,224, filed May 13, 2016 the entire contents of which are hereby incorporated by reference as if fully set forth herein, under 35 U.S.C. § 119(e).

BACKGROUND

Treatment of hematological cancers such as myelomas, lymphomas and leukemias is very complex. Tremendous clinical variability among remissions is observed in hematological cancer subjects, even those that occur after one course of therapy. Subjects who are resistant to therapy have very short survival times, regardless of when the resistance occurs. A need exists for an effective means to treat hematological cancer and to improve the efficacy of current chemotherapies in those subjects resistant, refractory, or otherwise not responsive to treatment with such chemotherapies.

c-Myc is a master transcription factor and one of the most frequently altered genes across a vast array of human cancers [1]. Overexpression of c-Myc is observed in up to 30% of cases of diffuse large B-cell lymphoma (DLBCL) [2], the most common type of aggressive lymphoma. c-Myc overexpression in lymphoma is a relatively common, and highly unfavorable, pathogenetic factor in DLBCL. Strategies that target this pathway could markedly improve the outcome of patients with c-Myc overexpressing lymphomas and other hematologic cancers. To date no drugs that directly target c-Myc have been approved for the treatment of any cancer. In fact, since c-Myc is involved in many essential functions in normal cells, direct c-Myc inhibitors may theoretically be associated with significant toxicity. Alternatively, it may be advantageous to inhibit upstream cancer-specific signals that converge on c-Myc as a therapeutic strategy to mitigate the poor risks associated with c-Myc dysregulation in lymphoma.

BRIEF DESCRIPTION OF THE DRAWINGS

The present invention is illustrated by way of example, and not by way of limitation, in the figures of the accompanying drawings.

FIG. 1A shows that compared to the vehicle treated negative control sample, CUX-03166, as a single agent, reduced the viability to 0% at a 25 uM concentration after 48 hours of treatment. At a concentration of 50 uM, viability of cells drops to 0% just at 24 hours of treatment. FIG. 1B shows the results of cells that were treated with Cal-101 and TGR-1202 and viability was determined at 24 hours. For lower concentrations of 5 μm and 15 μM, viability dropped to ~0.80% for both treatments. However, as concentrations increased up to 50 μM, viability remained at ~80% for Cal-101 and modestly dropped to ~65% for TGR-1202.

DETAILED DESCRIPTION

1. Introduction

Figure 1:
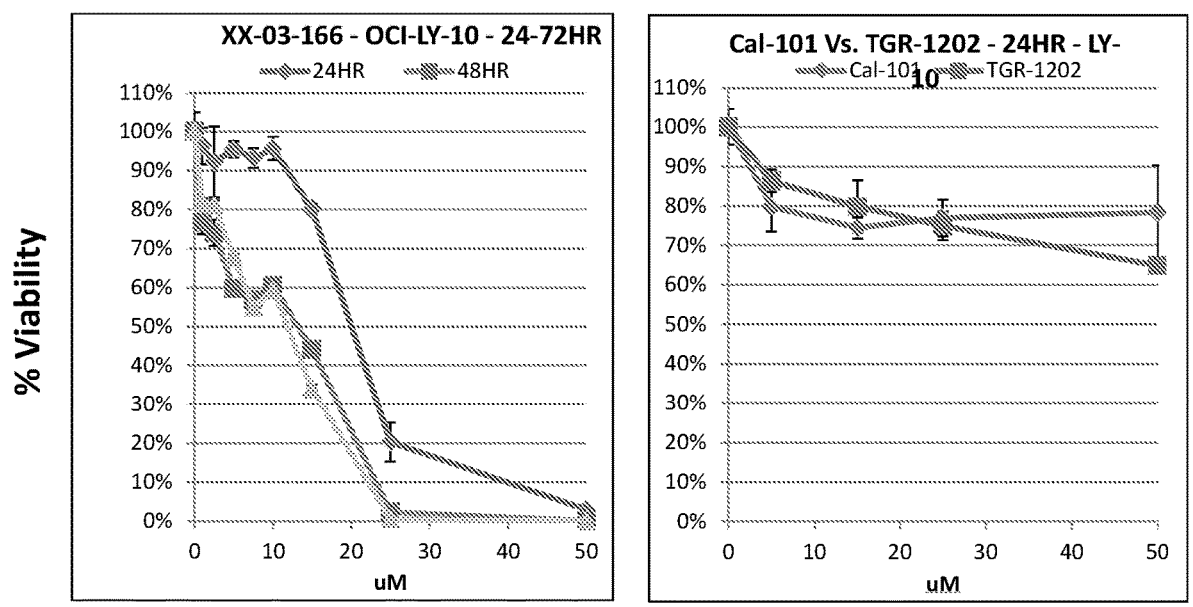
FIG. 1 CUX-03166 reduces viability of LY10 cells. The lymphoma cell line LY10 was treated with CUX-03166 for 24 hours, 48 hours and 72 hours.

The present invention is based on the development of compounds that dramatically reduce c-Myc in c-Myc over-expressing cancer cells. Accordingly, embodiments of the invention represent new therapies for treating c-Myc over-expressing cancers, particularly hematological cancers such as aggressive B- and T-cell lymphomas. The compounds were discovered while attempting to develop PI3K inhibitors that possess higher inhibitory potential. Many of the enumerated compounds taught herein have weak PI3K inhibition, but, surprisingly, are capable of reducing c-Myc in lymphoma cells and at lower concentrations compared to known PI3K inhibitors.

In certain embodiments, the c-Myc reducing compounds are defined by Formulas I and II below:

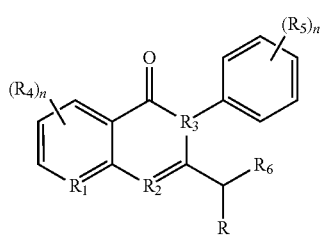

Formula I

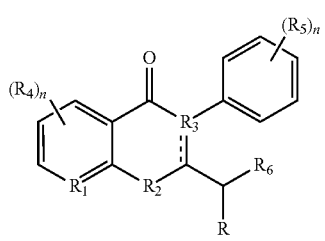

Formula II wherein
R is H or any one of groups A-G:

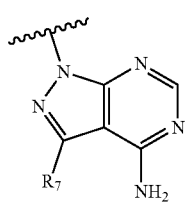

A

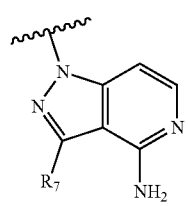

B

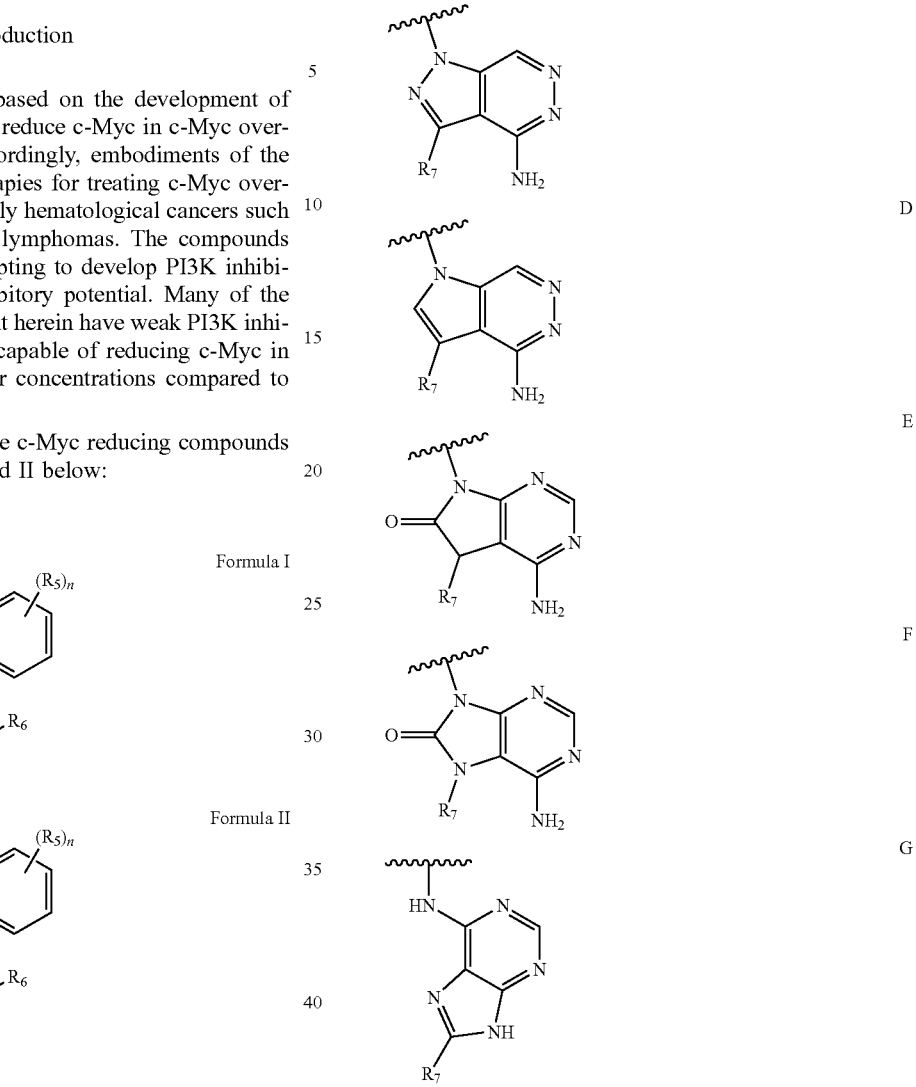

and wherein
═════ represents a single or double bond;
$R_1$ is CH, substituted C or N;
$R_2$
  in the compound of Formula I is CH, substituted C or N;
  in the compound of Formula II is O, $CH_2$, substituted C, NH or substituted N;
$R_3$
  in the compound of Formula I is CH, substituted C or N;
  in the compound of Formula II is
    CH, substituted C or N when ═════ represents a single bond; or
    C when ═════ represents a double bond;
each $R_4$ is independently substituted alkyl, unsubstituted alkyl, substituted alkenyl, unsubstituted alkenyl, substituted alkynyl, unsubstituted alkynyl, or halogen;
each $R_5$ is independently substituted alkyl, unsubstituted alkyl, substituted alkenyl, unsubstituted alkenyl, substituted alkynyl, unsubstituted alkynyl, or halogen;
$R_6$ is substituted $C_{2-10}$alkyl or unsubstituted $C_{2-10}$alkyl, or $C_{1-10}$alkyl or unsubstituted $C_{1-10}$alkyl if $R_1$, $R_2$, and $R_3$ are N or if $R_4$ is aminoalkyl or aminodialkyl;

$R_7$ is H or a group selected from any one of groups J, K and H

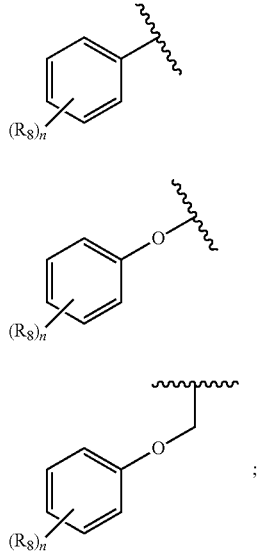

and each $R_8$ is independently substituted alkyl, unsubstituted alkyl, substituted O-alkyl, unsubstituted O-alkyl or halogen;

n, for $R_4$ and when $R_1$ is not N, is 0, 1, 2, 3 or 4;

for $R_4$ and when $R_1$ is N, is 0, 1, 2 or 3;

for $R_5$ is 0, 1, 2, 3, 4 or 5;

for $R_8$ is 0, 1, 2, 3, 4 or 5;

with the provisos that $R_7$ is not H when R is group G and either $R_3$ is not N or $R_4$ is not aminoalkyl or aminodialkyl; and the following compound is excluded:

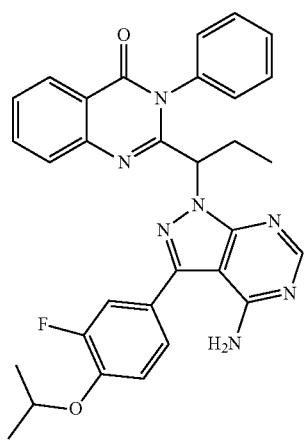 [SMILES: CCC(c1nc2ccccc2c(=O)n1-c1ccccc1)n1nc(-c2ccc(OC(C)C)c(F)c2)c2c(N)ncnc21]

In a more specific embodiment, the enumerated compound is designated as CUX-03166 with the following structure:

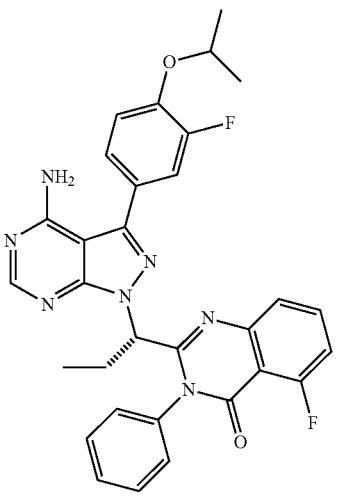

In another more specific embodiment, the enumerated compound is designated as CUX-0404A with the following structure:

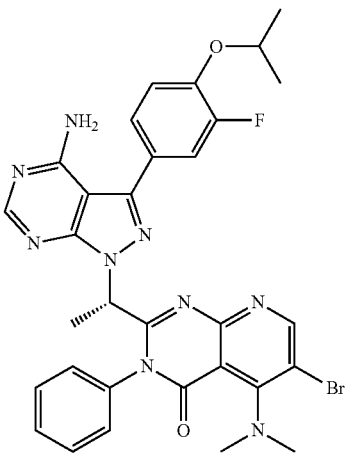

Other embodiments relate to treating a c-Myc overexpressing cancer in a subject by administering a c-Myc reducing amount of the c-Myc reducing agent. In an alternative embodiment, the c-Myc reducing agent is co-administered with one or more adjunct c-Myc inhibitors or one or more adjunct cancer therapeutic agents. In specific embodiments, the adjunct c-Myc inhibitors are a PI3K inhibitor, dual PI3K/CK-1 inhibitor, proteasome inhibitor, and/or CK-1 inhibitor. The c-Myc reducing agent may be provided as a lead-in treatment to reduce or initiate reduction of c-Myc prior to administration of the adjunct cancer therapeutic agent. Treatment with a c-Myc reducing agent modulates the disease state of the c-Myc overexpressing cancer making it less malignant and more susceptible to adjunctive cancer therapies.

2. Definitions

Unless otherwise defined, all technical and scientific terms used herein are intended to have the same meaning as commonly understood in the art to which this invention pertains and at the time of its filing. Although various methods and materials similar or equivalent to those described herein can be used in the practice or testing of the present invention, suitable methods and materials are described below. However, the skilled should understand that the methods and materials used and described are examples and may not be the only ones suitable for use in the invention. Moreover, it should also be understood that as measurements are subject to inherent variability, any temperature, weight, volume, time interval, pH, salinity, molarity or molality, range, concentration and any other measurements, quantities or numerical expressions given herein are intended to be approximate and not exact or critical figures unless expressly stated to the contrary. Hence, where appropriate to the invention and as understood by those of skill in the art, it is proper to describe the various aspects of the invention using approximate or relative terms and terms of degree commonly employed in patent applications, such as: so dimensioned, about, approximately, substantially, essentially, consisting essentially of, comprising, and effective amount.

Generally, nomenclature used in connection with, and techniques of, cell and tissue culture, molecular biology, immunology, microbiology, genetics, protein, and nucleic acid chemistry and hybridization described herein are those well-known and commonly used in the art. The methods and techniques of the present invention generally are performed according to conventional methods well known in the art and as described in various general and more specific references, unless otherwise indicated. See, e.g., Sambrook et al., Molecular Cloning: A Laboratory Manual, 2d ed., Cold Spring Harbor Laboratory Press, Cold Spring Harbor, N.Y. (1989); Ausubel et al., Current Protocols in Molecular Biology, Greene Publishing Associates (1992, and Supplements to 2002); Harlow and Lan, Antibodies: A Laboratory Manual, Cold Spring Harbor Laboratory Press, Cold Spring Harbor, N.Y. (1990); Kandel, Schwartz, and Jessell, eds., Principles of Neural Science, 4th ed., McGraw-Hill/Appleton & Lange: New York, N.Y. (2000). Unless defined otherwise, all technical and scientific terms used herein have the same meaning as commonly understood by one of ordinary skill in the art.

As used herein and in the appended claims, the singular forms "a," "an," and "the" include plural references unless the content clearly dictates otherwise.

The term "about" as used herein means approximately, roughly, around, or in the region of. When the term "about" is used in conjunction with a numerical range, it modifies that range by extending the boundaries above and below the numerical values set forth. In general, the term "about" is used herein to modify a numerical value above and below the stated value by a variance of 20% up or down (higher or lower).

The terms "subject," "individual," "host," and "patient," are used interchangeably herein to refer to an animal being treated with one or more enumerated agents as taught herein, including, but not limited to, simians, humans, avians, felines, canines, equines, rodents, bovines, porcines, ovines, caprines, mammalian farm animals, mammalian sport animals, and mammalian pets. A suitable subject for the invention can be any animal, preferably a human, that is suspected of having, has been diagnosed as having, or is at risk of developing a disease that can be ameliorated, treated or prevented by administration of one or more enumerated agents.

The term "administering" an agent as used herein means providing the agent to a subject using any of the various methods or delivery systems for administering agents or pharmaceutical compositions known to those skilled in the art.

The term "co-administration" or "co-administering" as used herein refers to the administration of an active agent before, concurrently, or after the administration of another active agent such that the biological effects of either agents overlap. The combination of agents as taught herein can act synergistically to treat or prevent the various diseases, disorders or conditions described herein. Using this approach, one may be able to achieve therapeutic efficacy with lower dosages of each agent, thus reducing the potential for adverse side effects.

The term "cancer" or "tumor" as used herein means is intended to include any neoplastic growth in a patient, including an initial tumor and any metastases. The cancer can be of the liquid or solid tumor type. Liquid tumors include tumors of hematological origin (hematological cancer), including, e.g., myelomas (e.g., multiple myeloma), leukemias (e.g., Waldenstrom's syndrome, chronic lymphocytic leukemia, other leukemias), and lymphomas (e.g., B-cell lymphomas, non-Hodgkins lymphoma). Solid tumors can originate in organs, and include cancers such as lung, breast, prostate, ovary, colon, kidney, and liver. In a specific embodiment, cancer pertains to c-Myc overexpressing cancer.

The term "cancerous cell" or "cancer cell" as used herein means a cell that shows aberrant cell growth, such as increased cell growth. A cancerous cell may be a hyperplastic cell, a cell that shows a lack of contact inhibition of growth in vitro, a tumor cell that is incapable of metastasis in vivo, or a metastatic cell that is capable of metastasis in vivo. Cancer cells include, but are not limited to, carcinomas, such as myelomas, leukemias (e.g., acute myelogenous leukemia, chronic lymphocytic leukemia, granulocytic leukemia, monocytic leukemia, lymphocytic leukemia), and lymphomas (e.g., follicular lymphoma, mantle cell lymphoma, diffuse large B-cell lymphoma, malignant lymphoma, plasmocytoma, reticulum cell sarcoma, or Hodgkins disease).

The terms "cancerous B cell" and "cell of aB-cell cancer" are used interchangeably herein to refer to a B cell that is cancerous.

The terms "hematological cancer" or "hematological malignancies" are used interchangeably and pertain to malignant neoplasms that derive from either of the two major blood cell lineages: myeloid and lymphoid cell lines. The myeloid cell line normally produces granulocytes, erythrocytes, thrombocytes, macrophages and mast cells; the lymphoid cell line produces B, T, NK and plasma cells. Lymphomas, lymphocytic leukemias, and myeloma are from the lymphoid line, while acute and chronic myelogenous leukemia, myelodysplastic syndromes and myeloproliferative diseases are myeloid in origin.

The term "enumerated disease," as used herein, refers to any cancer or other disease described herein as being treatable using embodiments of the invention; more specifically it includes myelomas (e.g. multiple myeloma), leukemias (e.g., acute myelogenous leukemia, chronic lymphocytic leukemia, granulocytic leukemia, monocytic leukemia, lymphocytic leukemia), and lymphomas (e.g., follicular lymphoma, mantle cell lymphoma, diffuse large B-cell lymphoma, malignant lymphoma, plasmocytoma, reticulum cell sarcoma, or Hodgkins disease).

The term "treating" or "treatment of," as used herein, refers to providing any type of medical management to a subject. Treating includes, but is not limited to, administering a composition comprising one or more active agents to a subject using any known method for purposes such as curing, reversing, alleviating, reducing the severity of, inhibiting the progression of, or reducing the likelihood of a disease, disorder, or condition or one or more symptoms or manifestations of a disease, disorder or condition.

A "therapeutically effective amount" refers to an amount which, when administered in a proper dosing regimen, is sufficient to reduce or ameliorate the severity, duration, or progression of the disorder being treated (e.g., cancer), prevent the advancement of the disorder being treated, cause the regression of the disorder being treated, or enhance or improve the prophylactic or therapeutic effects(s) of another therapy. The full therapeutic effect does not necessarily occur by administration of one dose and may occur only after administration of a series of doses. Thus, a therapeutically effective amount may be administered in one or more administrations per day for successive days.

The term "phosphoinositide 3-kinase (PI3K) inhibitor(s)" as used herein includes agents that block or reduce expression or activity of PI3K. Examples of PI3K inhibitors are provided in Table 1. PI3K inhibitors for use in embodiments of the invention are also described in U.S. Pat. Nos. 8,642,607; 8,912,331; and 9,018,375. In a specific embodiment, the PI3K inhibitor inhibits PI3Kδ.

The term "proteasome(s)" as used herein refers to protein complexes inside eukaryotes that are located in the nucleus and the cytoplasm that function to degrade unneeded or damaged proteins by proteolysis. Proteasomes are abundant multi-enzyme complexes that provide the main pathway for degradation of intracellular proteins and contribute to the maintenance of protein homeostasis and clearance of misfolded and/or unfolded and cytotoxic proteins. The ubiquitin-proteasome pathway (UBP) modulates intracellular protein degradation. Specifically, the 26S proteasome is a multi-enzyme protease that degrades misfolded or redundant proteins; conversely, blockade of the proteasomal degradation pathways results in accumulation of unwanted proteins and cell death. Because cancer cells are more highly proliferative than normal cells, their rate of protein translation and degradation is also higher. Thus, cancer cells are more dependent on the proteasome for clearance of abnormal or mutant proteins than normal cells.

The term "proteasome inhibitor(s)" as used herein pertains to an agent(s) that blocks or reduces the action of proteasomes. Examples of proteasome inhibitors are provided in the Therapeutic Agents section provided below.

The term "c-Myc" as used herein means the transcription factor encoded by the proto-oncogene c-myc that controls cell proliferation. c-Myc also plays a role in regulating cell cycle, cell growth, angiogenesis, apoptosis, and oncogenesis. The c-Myc transcription factor is of the helix-loop-helix leucine zipper class and plays a role in the modulation and initiation of transcription. c-Myc binds to E-boxes (CACGTG) in the vicinity of target genes, which are then activated. The DNA binding activity requires dimerization with another helix-loop-helix leucine zipper protein called Max. Max can also interact with transcriptional repressors such as Mad and Mxi1, which presumably down-regulate expression of c-Myc target genes. c-Myc, when activated, can induce malignancy in a variety of tissues, most notably hematopoietic tissues (Leder et al., 222 Science 765, 1983). Myc's activity can increase in tumors as a consequence of mutations, chromosomal rearrangements, increased expression, or gene amplification. Elevated or deregulated expression of c-Myc has been detected in a wide range of human cancers and is often associated with aggressive, poorly differentiated tumors. Such cancers include colon, breast, cervical, small-cell lung carcinomas, osteosarcomas, glioblastomas, melanoma and myeloid leukemias.

The term "n-Myc" as used herein means the n-Myc proto-oncogene protein that is a protein encoded by the MYCN gene. The terms n-Myc, MYCN or NMYC are used interchangeably herein. The gene is a member of the MYC family of transcription factors. The expressed protein contains a basic helix-loop-helix domain and must dimerize with another basic helix-loop-helix domain to bind DNA. Like c-Myc, the MYCN protein interacts with MAX. Amplification of the MYCN gene is mostly associated with a variety of tumors, most notably neuroblastomas.

The term "CK-1 inhibitor" as used herein refers to agents that block or reduce expression or activity of CK-1. Examples of CK-1 inhibitors are provided in Table 3. Dual PI3K/CK-1 inhibitors are a subclass of CK-1 inhibitors and are therefore encompassed by the term CK-1 inhibitor, unless otherwise specified.

The term "CK-1 reducing effective amount" as used herein means an amount of a CK-1 inhibitor administered to a subject that reduces activity of CK-1 in the subject by at least 30, 40, 50 or 60 percent of its normal activity.

The term "c-Myc overexpressing cancer" as used herein relates to any cancer wherein the cancer cells overexpress c-Myc as compared to normal, healthy cells. Overexpression of c-Myc includes elevated RNA transcript or protein levels of c-Myc as compared to healthy, normal cells. c-Myc overexpressing cancers comprise hematological cancers such as, myelomas (e.g. multiple myeloma), leukemias (e.g., acute myelogenous leukemia, chronic lymphocytic leukemia, granulocytic leukemia, monocytic leukemia, lymphocytic leukemia), lymphomas (e.g., follicular lymphoma, mantle cell lymphoma, diffuse large B-cell lymphoma, malignant lymphoma, plasmocytoma, reticulum cell sarcoma, or Hodgkins disease) and solid-tumor cancers of the lung, breast, prostate, ovary, colon, kidney, and liver.

The term "c-Myc reducing amount" as used herein means an amount of an enumerated agent administered to a subject that reduces a level of c-Myc in cells of a subject.

The term "AKT inhibitor" as used herein refers to agents that block or reduce expression or activity of AKT. A non-limiting list of AKT inhibitor examples is provided in Table 1.

The term "mTOR inhibitor" as used herein refers to agents that block or reduce expression or activity of mTOR. A non-limiting list of mTOR inhibitor examples is provided in Table 1.

The term "PI3K-AKT-mTOR signaling pathway inhibitor" refers to any of a PI3K inhibitor, dual PI3K/CK-1 inhibitor, AKT inhibitor, or mTOR inhibitor. A non-limiting list of examples of these inhibitors is provided in Table 1.

The term "dual PI3K/CK-1 inhibitor" as used herein includes agents that reduce the biological activity or expression of both PI3K and at least one isoform of CK-1. Typically, a dual PI3K/CK-1 inhibitor reduces activity of PI3Kδ and CK-1α, δ and/or ε. Dual inhibition of PI3K with CK1 ε has been shown to have a strong synergistic effect of killing cancer cells in conjunction with proteasome inhibitor administration.

The term "adjunct c-Myc inhibitor" refers to any of a PI3K-AKT-mTOR signaling pathway inhibitor, proteasome inhibitor or CK-1 inhibitor.

The term "enumerated therapeutic agent(s)" or "enumerated agents" as used herein refers to any of a c-Myc reducing agent, an adjunct-c-Myc inhibitor, or adjunct cancer therapeutic agent. Enumerated therapeutic agents may include analogs, derivatives or pharmaceutically acceptable salts of any agent specified herein.

As used herein, an "adjunct cancer therapeutic agent" pertains to an agent that possesses selectively cytotoxic or cytostatic effects on cancer cells over normal cells. Adjunct cancer therapeutic agents may be co-administered with a CK-1 inhibitor, dual PI3K/CK-1 inhibitor or a combination of a PI3K-AKT-mTOR signaling pathway inhibitor and CK-1 inhibitor, optionally with a proteasome inhibitor. A non-limiting list of examples of adjunct cancer therapeutic agents is provided in Table 2.

As used herein, the term "adjunct cancer therapy protocol" refers to a therapy, such as surgery, chemotherapy, radiotherapy, thermotherapy, and laser therapy, and may provide a beneficial effect when administered in conjunction with administration of a CK-1 inhibitor, dual PI3K/CK-1 inhibitor and/or a combination of a PI3K-AKT-mTOR inhibitor and CK-1 inhibitor, and any of the foregoing optionally including a proteasome inhibitor. Such beneficial effects include reducing tumor size, slowing rate of tumor growth, inhibiting metastasis, or otherwise improving overall clinical condition, without necessarily eradicating the cancer. Cytostatic and cytotoxic agents that target the cancer cells are specifically contemplated for combination therapy. Likewise, agents that target angiogenesis or lymphangiogenesis are specifically contemplated for combination therapy.

3. Overview c-Myc is a master transcription factor and one of the most frequently altered genes across a vast array of human cancers [1]. Overexpression of c-Myc is observed in up to 30% of cases of diffuse large B-cell lymphoma (DLBCL) [2], the most common type of aggressive lymphoma. Although DLBCL can be cured in 60-70% patients [3], a substantial minority of patients with DLBCL still die from their lymphoma. DLBCL can be divided by gene-expression profiling (GEP) studies into germinal center B cell-like (GCB) and activated B cell-like (ABC) subtypes. While the ABC subtype has an inferior prognosis compared to the GCB subtype [4], there is emerging evidence that c-Myc overexpression is an independent risk factor in both subtypes.

The most common mechanism of c-Myc activation is translocation to any of the immunoglobulin (Ig) or T cell receptor loci during lymphoid maturation. For example, in Burkitt's lymphoma the c-Myc locus on chromosome 8 translocates most often to the Ig heavy chain locus on chromosome 14, but also to the lambda or kappa light chain Ig genes on chromosomes 2 and 22 (Magrath, in "Epstein-Barr Virus and Associated Diseases," M. Nijhoff Publishing: 631, 1986). In some instances the c-Myc transcription region is altered in the non-coding exon 1 region; in such cases transcription is initiated at a cryptic promoter present in the first intron of the c-Myc locus.

Early studies by Savage [5] and Barrans [6] reported that 9% to 14% patients with newly diagnosed DLBCL harbor a c-Myc gene rearrangement. In patients treated with the regimen R-CHOP (Rituximab, Cyclophosphamide, Hydroxydaunorubicin (doxorubicin), Oncovin (vincristine), and Prednisone), c-Myc gene rearrangement was associated with an inferior overall survival that is only half of that for patients without c-Myc translocation. Subsequently Johnson [7], Green [8], and Hu [9] independently observed a similar frequency of c-Myc rearrangement (10-15%) and a significantly higher frequency (30%) of c-Myc protein expression in large sample sets of newly diagnosed DLBCL patients. Further, these later studies demonstrated that the poor survival associated with dysregulated c-Myc was present only when another oncogene, Bcl2, is also overexpressed. DLBCL with coexpression of the c-Myc and Bcl-2 proteins, i.e. double positive (DP)-DLBCL, is significantly enriched with the ABC than the GCB subtype, and appears to be the primary cause of the relatively poor survival of the ABC subtype. "Double hit" lymphoma (DHL) represents 5% of all DLBCL [10], and is characterized by chromosome rearrangements involving both c-Myc and Bcl2. DLBCL exhibits an even worse prognosis than DP-DLBCL [11], and intriguingly, demonstrates an immunohistochemical staining consistent with the GCB subtype in most cases [12].

The c-Myc protein has a short half-life, less than 30 minutes [13]. and needs to be produced constantly in c-Myc driven cancers. The complex secondary structure of the 5' untranslated region (UTR) of c-Myc makes its translation highly dependent on the eukaryotic initiation factor 4F (eIF4F) [14, 15]. eIF4F exists as a complex comprised of eIF4E, eIF4A, and eIF4G. eIF4E is the rate limiting factor for eIF4F, as eIF4E can be sequestered by 4EBP1 [16]. The mammalian target of rapamycin (mTOR) causes phosphorylation dependent inactivation of 4EBP1, leading to release of eIF4E from 4EBP1 and assembly of the eIF4F complex. mTOR is activated through the PI3K-AKT pathway. Furthermore, the ubiquitin-proteasome system is also critically involved in the activation of mTOR [17-19]. Conversely, activated mTOR can increase the levels of intact and active proteasomes through a global increase in the expression of genes encoding proteasome subunits [20].

c-Myc itself can act as an upstream stimulator of mTOR [21], and is required for the transcription of the eIF4F subunits [14]. It has been observed that mTOR acts as a nexus that coordinates complex upstream signals to stimulate eIF4F dependent translation of c-Myc.

For many years c-Myc has been the prototypical example of an "undruggable" oncogene. Increased understanding of the role of bromodomains in mediating protein-protein interaction on the chromatin has created new opportunities in down-regulating transcriptional activators [30-36].

A few BRD4 inhibitors have entered small phase I clinical studies, but the safety and toxicity data are not available yet. Seminal work by Pelletier's group discovered an eIF4F-Myc feed-forward loop whereby eIF4F stimulates the translation of c-Myc, and c-Myc enhances the transcription of eIF4F subunits [14]. The inventors have realized that the interdependence of eIF4F and c-Myc creates another opportunity to inhibit the oncoprotein. Recently, a number of small molecule inhibitors have been identified that inhibit either the activity or interaction of eIF4F subunits and cofactors, leading to down-regulation of c-Myc, direct killing of cancer cells, and enhanced sensitivity of cancer cells to chemotherapeutic agents in cell line and animal models [14, 15, 37-42]. None of these eIF4F inhibitors have entered clinical development.

4. Summary of the Results

The following is a summary of results of experiments described in the Examples of this application.
- CUX-03166 was developed as an analog of TGR-1202 PI3KKδ inhibitor and shares structural similarity to TGR-1202;
- CUX-03166 reduced viability of lymphoma cells (lymphoma cell line LY10) and showed 0% viability at 50

μM after 24 hours, and this reduction in viability was dramatically greater than TGR-1202 (65% viability) and Cal-101 (80% viability);

CUX-03166 reduced viability of lymphoma cells (lymphoma cell line LY7): at 15 uM concentrations, viability of cells dropped to 40% at 24 hours, 10% at 48 hours, and ~0% at 72 hours, and at 25 uM concentrations, viability dropped to 0% at 24 hours; and CUX-03166 showed a fiftyfold greater potency at reducing c-Myc compared to TGR-1202 in LY7 cells.

CUX-0404A reduced viability of lymphoma cells (lymphoma cell line LY10) and showed 0% viability at 25 μM and 20 μM after 24 hours and 48 hours, respectively;

CUX-0404A reduced viability of lymphoma cells (mantle cell lymphoma) and showed 20% viability at 25 μM after 24 hours, and this reduction in viability was dramatically greater than TGR-1202 (60% viability);

CUX-0404A dramatically reduced c-myc at 20 μM in LY7 cells.

CUX-0404A inhibited CK1epsilon but was less potent at inhibiting CK1epsilon than TGR-1202.

5. Detailed Description of Embodiments

Therapeutic Agents
c-Myc Reducing Agents c-Myc reducing agents used in therapeutic methods for treating c-Myc overexpressing cancers or hematologic cancers include the following:

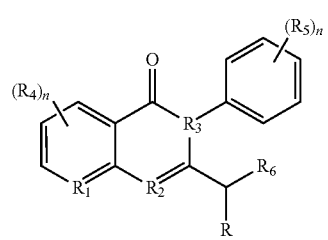

Formula I

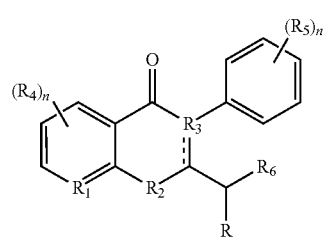

Formula II wherein
R is H or any one of groups A-G:

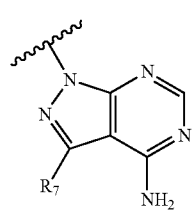

A

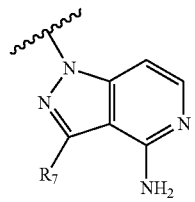

B

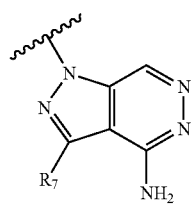

C

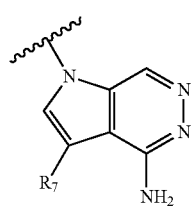

D

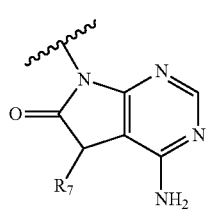

E

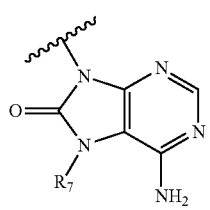

F

G and wherein
------ represents a single or double bond;
$R_1$ is CH, substituted C or N;
$R_2$
   in the compound of Formula I is CH, substituted C or N;
   in the compound of Formula II is O, $CH_2$, substituted C, NH or substituted N;
$R_3$
   in the compound of Formula I is CH, substituted C or N;
   in the compound of Formula II is
     CH, substituted C or N when ------ represents a single bond; or
     C when ------ represents a double bond;

each $R_4$ is independently substituted alkyl, unsubstituted alkyl, substituted alkenyl, unsubstituted alkenyl, substituted alkynyl, unsubstituted alkynyl, or halogen;

each $R_5$ is independently substituted alkyl, unsubstituted alkyl, substituted alkenyl, unsubstituted alkenyl, substituted alkynyl, unsubstituted alkynyl, or halogen;

$R_6$ is substituted $C_{2-10}$alkyl or unsubstituted $C_{2-10}$ alkyl;

$R_7$ is H or a group selected from any one of groups J, K and H;

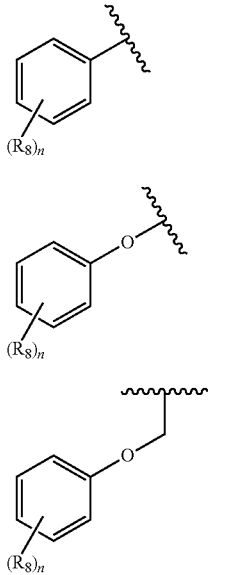

and each $R_8$ is independently substituted alkyl, unsubstituted alkyl, substituted O-alkyl, unsubstituted O-alkyl or halogen;

n,
for $R_4$ and when $R_1$ is not N, is 0, 1, 2, 3 or 4;
for $R_4$ and when $R_1$ is N, is 0, 1, 2 or 3;
for $R_5$ is 0, 1, 2, 3, 4 or 5;
for $R_8$ is 0, 1, 2, 3, 4 or 5;

with the provisos that
$R_7$ is not H when R is group G;
the following compound is excluded:

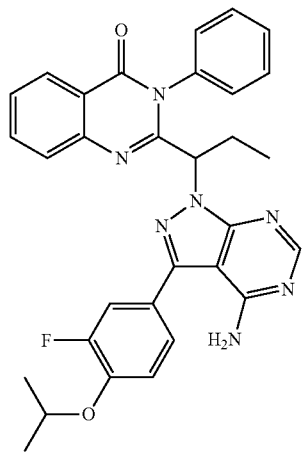 [SMILES: CCC(c1nc2ccccc2c(=O)n1-c1ccccc1)n1nc(-c2ccc(OC(C)C)c(F)c2)c2c(N)ncnc21]

c-Myc reducing agents include compounds of Formulas I and II above, and analogs or derivatives thereof, or pharmaceutically acceptable salts thereof.

In specific embodiments, the following compounds are excluded from Formula I and II:

compounds of formula I wherein at the same time R is group A, $R_1$ is CH, $R_3$ is N and $R_7$ is J;

compounds of formula II wherein at the same time R is group A, $R_1$ is CH, $R_2$ is O, $R_3$ is C, ====== represents a double bond, and $R_7$ is J.

In other specific embodiments, one or more of the following apply to Formulas I and II:

$R_6$ is substituted $C_{3-10}$alkyl or unsubstituted $C_{3-10}$alkyl.

$R_6$ is substituted or unsubstituted propyl or substituted or unsubstituted butyl.

$R_6$ is substituted or unsubstituted ethyl.

$R_1$ is N.

$R_2$ is not O.

$R_3$ is not N.

$R_4$ is halogen and n for $R_4$ is 1 or 2.

$R_4$ is F and n for $R_4$ is 1 or 2.

$R_4$ is F, n for $R_4$ is 1, and $R_4$ is located at position 5 of the quinazolin-4-one ring to which it is attached.

n for $R_5$ is O.

$R_6$ is Me.

R is not group A.

R is group A.

$R_7$ is J.

$R_7$ is not J.

n for $R_8$ is 2, one $R_8$ is isopropyl or O-isopropyl, and the other $R_8$ is halogen, preferably F.

In other embodiments, $R_7$ is one of the following:

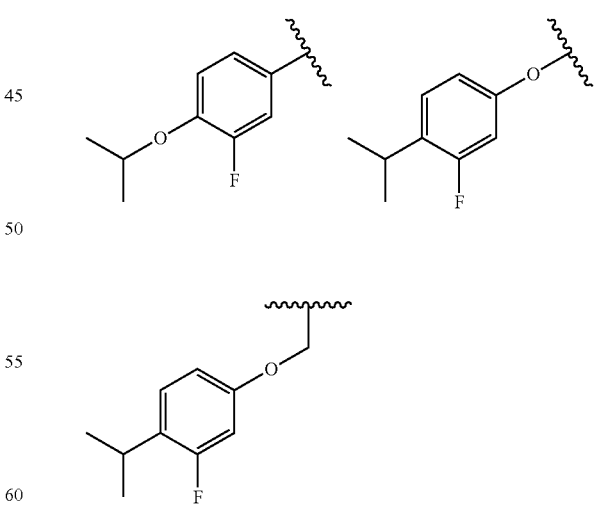

In a particular embodiment, the c-Myc reducing agent is a compound according to the following Formula III, or analogs or derivatives thereof, or pharmaceutically acceptable salts thereof:

Formula III

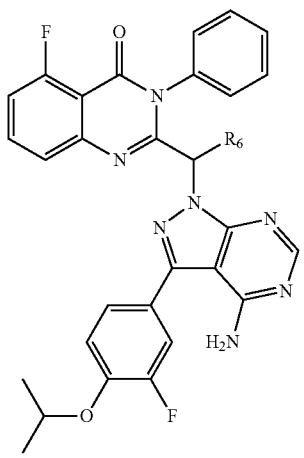

wherein R$_6$ is substituted C$_{2-10}$alkyl or unsubstituted C$_{2-10}$alkyl.

In other specific embodiments, the following apply to Formula III:

R$_6$ is substituted C$_{3-10}$alkyl or unsubstituted C$_{3-10}$alkyl;

R$_6$ is substituted or unsubstituted propyl or substituted or unsubstituted butyl;

R$_6$ is substituted or unsubstituted ethyl; or

R$_6$ is unsubstituted ethyl.

In a specific embodiment, the c-Myc reducing agent is CUX-03166. CUC-03166 may be made according to the following synthesis scheme:

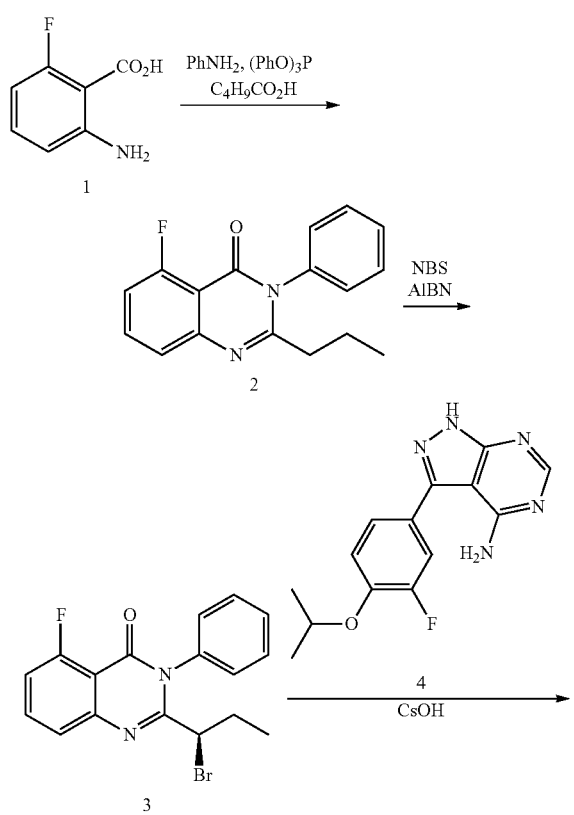

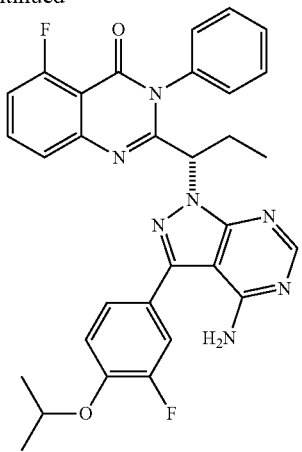

Compounds according to formulas I, II, and III may be prepared by employing and/or adapting synthetic methodology described in PCT publication Nos. WO2015001491, WO2008/127226, WO2009/088986, WO 2011/055215 and WO 2012/151525, which are incorporated herein by reference. Those skilled in the art would be able to modify the preparation schemes of these references within common general knowledge to produce such compounds.

Other embodiments of c-myc reducing agents include agents as follows: Formula I or Formula II:

Formula I

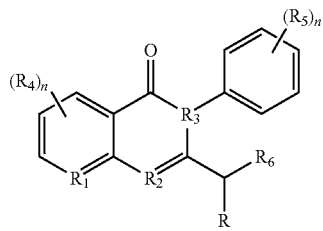

Formula II

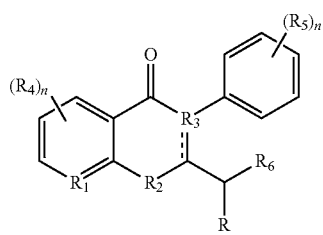

wherein
R is H or any one of groups A-G:

A

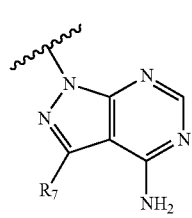

-continued

B
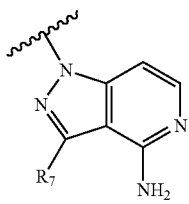

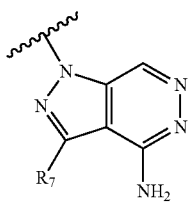

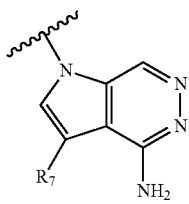

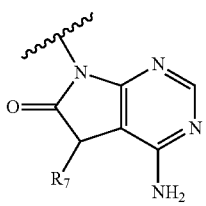

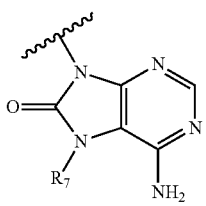

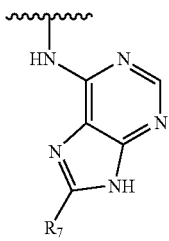

and wherein
===== represents a single or double bond;
$R_1$, $R_2$, and $R_3$ are N;
$R_4$ is each independently substituted alkyl, unsubstituted alkyl, substituted alkenyl, unsubstituted alkenyl, substituted alkynyl, unsubstituted alkynyl, aminoalkyl, aminodialkyl, or halogen;
$R_5$ is each independently substituted alkyl, unsubstituted alkyl, substituted alkenyl, unsubstituted alkenyl, substituted alkynyl, unsubstituted alkynyl, or halogen;
$R_6$ is substituted $C_{1-10}$alkyl or unsubstituted $C_{1-10}$alkyl;
$R_7$ is H or a group selected from any one of groups J, K and H

J

B

C

D

E and $R_8$ is each independently substituted alkyl, unsubstituted alkyl, substituted O-alkyl, unsubstituted O-alkyl or halogen;
n for $R_4$ and when $R_1$ is not N, is 0, 1, 2, 3 or 4;
n for $R_4$ and when $R_1$ is N, is 0, 1, 2 or 3;
n for $R_5$ is 0, 1, 2, 3, 4 or 5; and
n for $R_8$ is 0, 1, 2, 3, 4 or 5.

F

In specific embodiments, one or more of the following apply to the formula I and II when $R_1$, $R_2$, and $R_3$ are N:
$R_6$ is methyl.
n for $R_4$ is 2.
$R_4$ is bromide and is —$N(CH_3)_2$.

Another embodiment of c-myc reducing agents pertain to the following:

G

A compound according to Formula I or Formula II:

Formula I
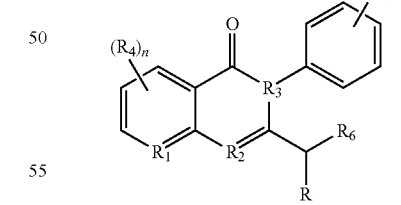

Formula II
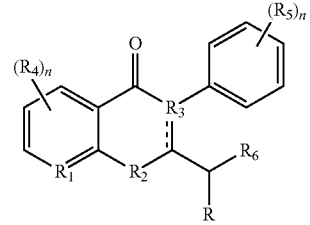

wherein
R is H or any one of groups A-G:

A 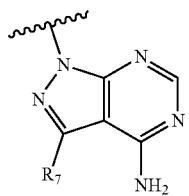

B 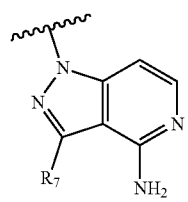

C 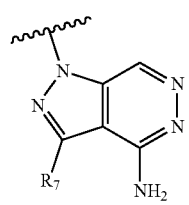

D 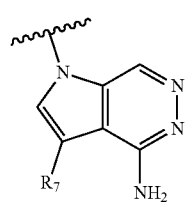

E 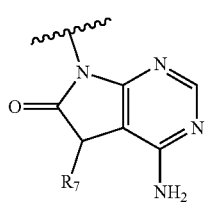

F 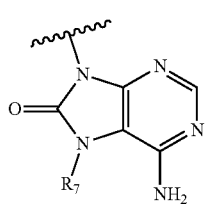

G 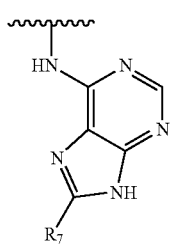

and wherein
- - - - - - represents a single or double bond;

$R_1$ is CH, substituted C or N;

$R_2$
in the compound of Formula I is CH, substituted C or N;
in the compound of Formula II is O, $CH_2$, substituted C, NH or substituted N;

$R_3$
in the compound of Formula I is CH, substituted C or N;
in the compound of Formula II is
CH, substituted C or N when ═══ represents a single bond; or
C when ═══ represents a double bond;

$R_4$ is each independently aminoalkyl or aminodialkyl, and optionally halogen;

$R_5$ is each independently substituted alkyl, unsubstituted alkyl, substituted alkenyl, unsubstituted alkenyl, substituted alkynyl, unsubstituted alkynyl, or halogen;

$R_6$ is substituted $C_{1-10}$alkyl or unsubstituted $C_{1-10}$alkyl;

$R_7$ is H or a group selected from any one of groups J, K and H

J 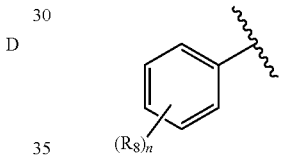

K 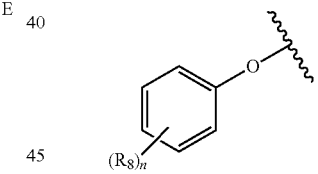

H 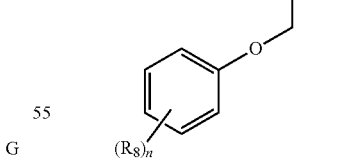

and
$R_8$ is each independently substituted alkyl, unsubstituted alkyl, substituted O-alkyl, unsubstituted O-alkyl or halogen;

n for $R_4$ and when $R_1$ is not N, is 0, 1, 2, 3 or 4;

n for $R_4$ and when $R_1$ is N, is 0, 1, 2 or 3;

n for $R_5$ is 0, 1, 2, 3, 4 or 5; and n for $R_8$ is 0, 1, 2, 3, 4 or 5.

In a specific embodiment, the c-myc reducing agent is

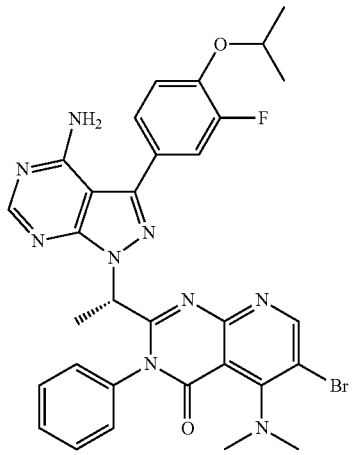

CUX-0404A

Synthesis Protocol for CUX-0404A

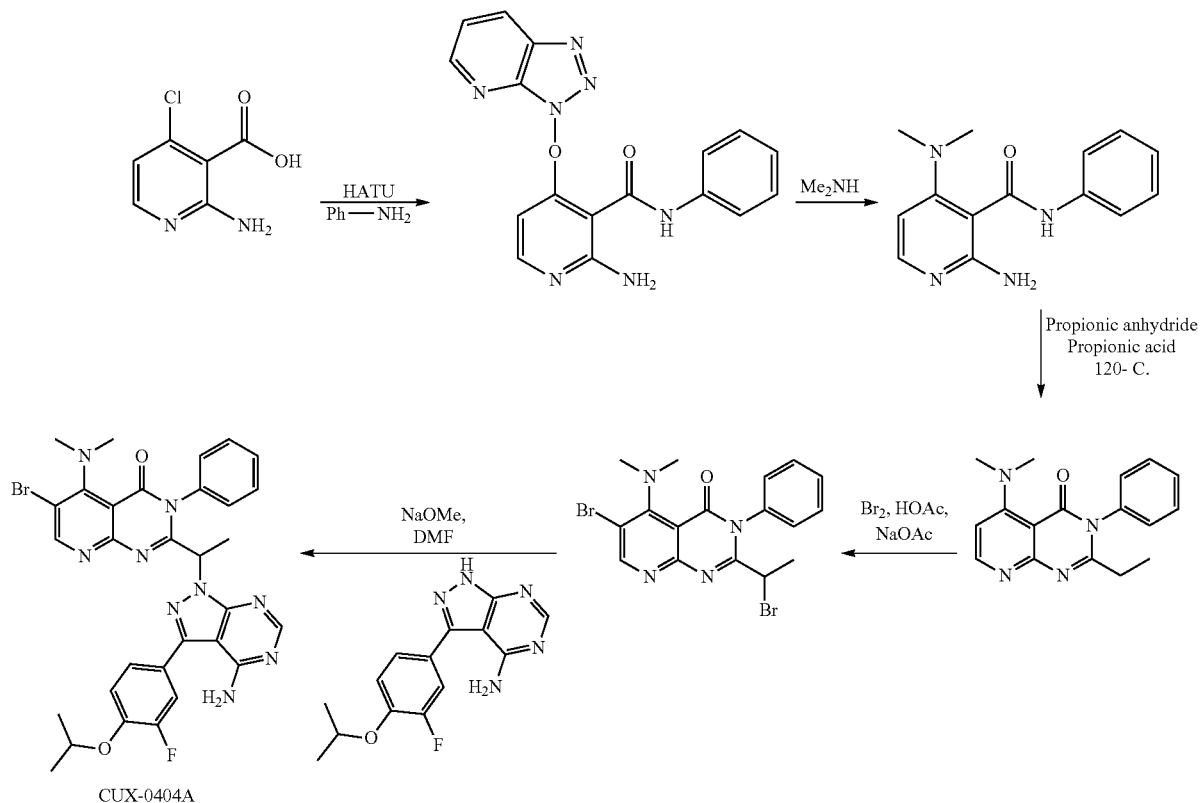

2-amino-4-chloronicotinic acid (50 mg) and aniline (0.026 mL) was dissolved in DMF (1 mL). Triethylamine (0.12 mL) and HATU (154 mg) was added to the solution and the reaction mixture was stirred at RT for 4 hours. The mixture was dried and purified twice by column (1st column: 10% methanol in DCM; 2nd column: Ethyl acetate) to yield 4-(3H-[1,233]triazolo[4,5-b]pyridin-3-yloxy)-2-amino-N-phenylnicotinamide (70 mg, 70%).

300 mg of the above product was dissolved in DMF (3 mL). Dimethylamine (0.6 g) was added and the resulting mixture was stirred at RT overnight and was dried in vacuo. The crude product 2-amino-4-(dimethylamino)-N-phenylnicotinamide was used for next step without purification.

Propionic acid (1.5 mL) and propionic anhydride (1.5 mL) were added to the above crude product and the mixture was stirred at 120° C. for 4 hours. The solvent was removed in vacuo and the crude product was purified by column chromatography with 8% methanol in DCM to yield the product 5-(dimethylamino)-2-ethyl-3-phenylpyrido[2,3-d]pyrimidin-4(3H)-one (178 mg, 70%).

168 mg of the above product was dissolved in acetic acid (1.5 mL). Sodium acetate (60 mg) and bromine (101 mg) was added, and the reaction mixture was stirred at RT overnight. The solvent was removed in vacuo and the crude product was dissolved in DCM and stirred with solid sodium bicarbonate. The reaction mixture was purified by column chromatography with 10% EtOAc in DCM to provide the dibromo compound (108 mg).

3-(3-fluoro-4-isopropoxyphenyl)-1H-pyrazolo[3,4-d]pyrimidin-4-amine (7.7 mg) was dissolved in ethanol (0.5 mL). Sodium methoxide (0.052 mL, 0.5 M in methanol) was added and the reaction mixture was stirred at RT for 30 minutes and was dried in vacuo to provide the crude sodium salt. The above dibromo compound (12 mg) was dissolved in DMF (0.5 mL) and was added to thus obtained sodium salt and the reaction mixture was stirred overnight. The reaction mixture was dried and purified by PTLC with 10% methanol in DCM to yield the CUX-0404A (10.4 mg, 59%).

Adjunct c-Myc Reducing Agents

In addition to the c-Myc reducing agents described above, other agents which reduce c-Myc (adjunct c-Myc inhibitors)

and are useful for treating c-Myc overexpressing cancers or hematologic cancers may be co-administered with the c-Myc reducing agents. Adjunct c-Myc inhibitors include any of a PI3K-AKT-mTOR signaling pathway inhibitor, proteasome inhibitor, or CK-1 inhibitor, including analogs or derivatives thereof, or pharmaceutically acceptable salts thereof. In select embodiments, adjunct c-Myc inhibitors include PI3K inhibitors, preferably those with dual PI3K and CK-1 inhibitory functions; proteasome inhibitors and inhibitors of various isoforms of CK-1, preferably CK-1ε where hematologic cancers and myeloma are being treated, including analogs or derivatives thereof, or pharmaceutically acceptable salts thereof. Tables 1 and 3 provide specific examples of PI3K inhibitors and CK-1 inhibitors, respectively, contemplated for use as anti-cancer agents.

Combinations of inhibitors can be used in co-administration therapy or in preparation of formulations, including, for example a combination of at least one c-Myc reducing agent and at least one adjunct c-Myc inhibitor, and optionally at least one adjunct cancer therapeutic agent. In a specific embodiment, the adjunct c-Myc inhibitor includes, but is not limited to, PI3K-AKT-mTOR signaling pathway inhibitor, proteasome inhibitor, or CK-1 inhibitor, including analogs or derivatives thereof, or pharmaceutically acceptable salts thereof. The PI3K-AKT-mTOR signaling pathway inhibitor is a dual PI3K/CK-1 inhibitor. In more specific embodiments, administration of a c-Myc reducing agent alone, or co-administration of a c-Myc reducing agent and an adjunct c-Myc inhibitor may be provided as a lead-in, c-Myc silencing treatment in a manner to reduce or initiate reduction of c-Myc prior to administration of the adjunct cancer therapeutic agent.

Proteasome Inhibitors

Examples of proteasome inhibitors useful in accord with the teachings herein include, but are not limited to, the following:

boronic ester or acid such as bortezomib (originally coded PS-341, and marketed as Velcade by Millennium Pharmaceuticals) is the approved name of the chemical entity [(1R)-3-methyl-1-({(2S)-3-phenyl-2-[(pyrazin-2-ylcarbonyl)amino]propanoyl}amino)butyl]boronic acid; or Ixazomib (MLN 2238); (R)-1-(2-(2,5-dichlorobenzamido)acetamido)-3-methylbutylboronic acid;

disulfiram [Disulfanediylbis(carbonothioylnitrilo)]tetraethane];

epigallocatechin-3-gallate (EGCG);

Salinosporamide A: 4R,5S)-4-(2-chloroethyl)-1-((1S)-cyclohex-2-enyl(hydroxy)methyl)-5-methyl-6-oxa-2-azabicyclo[3.2.0]heptane-3,7-dione;

Carfilzomib (PR-171); (S)-4-methyl-N—((S)-1-(((S)-4-methyl-1-((R)-2-methyloxiran-2-yl)-1-oxopentan-2-yl)amino)-1-oxo-3-phenylpropan-2-yl)-2-((S)-2-(2-morpholinoacetamido)-4-phenylbutanamido)pentanamide;

Oprozomib; (ONX-0912); O-methyl-N-[(2-methyl-5-thiazolyl)carbonyl]-L-seryl-O-methyl-N-[(1S)-2-[(2R)-2-methyl-2-oxiranyl]-2-oxo-1-(phenylmethyl)ethyl]-L-serinamide;

CEP-18770: [(1R)-1-[[(2S,3R)-3-hydroxy-2-[[(6-phenylpyridin-2-yl)carbonyl]amino]-1-oxobutyl]amino]-3-methylbutyl]boronic acid;

MLN9708: 4-(carboxymethyl)-2-((R)-1-(2-(2,5-dichlorobenzamido)acetamido)-3-methylbutyl)-6-oxo-1,3,2-dioxaborinane-4-carboxylic acid;

YU 101: (αS)-α-(acetylamino)benzenebutanoyl-L-leucyl-N-[(1S)-3-methyl-1-[[(2R)-2-methyl-2-oxiranyl]carbonyl]butyl]-L-phenylalaninamide;

Marizomib: (NPI-0052); (4R,5S)-4-(2-chloroethyl)-1-((1S)-cyclohex-2-enyl-(hydroxy)methyl)-5-methyl-6-oxa-2-azabicyclo[3.2.0]heptane-3,7-dione;

Epoxomicin: (2S,3S)—N-((2S,3R)-3-hydroxy-1-4(S)-4-methyl-1-((R)-2-methyloxiran-2-yl)-1-oxopentan-2-yl)amino)-1-oxobutan-2-yl)-3-methyl-2-((2S,3S)-3-methyl-2-(N-methylacetamido)pentanamido)pentanamide;

MG132: N-(benzyloxycarbonyl)leucinylleucinylleucinal Z-Leu-Leu-Leu-al; and

Lactacystin: 2-(acetylamino)-3-[({3-hydroxy-2-[1-hydroxy-2-methylpropyl]-4-methyl-5-oxopyrrolidin-2-yl}carbonyl)sulfanyl]propanoic acid.

See also, Crawford Li, Walker B, Irvine AE. Proteasome inhibitors in cancer therapy. *Journal of Cell Communication and Signaling.* 2011; 5(2):101-110. doi: 10.1007/s12079-011-0121-7.

PI3K Inhibitors

Examples of PI3K inhibitors useful for administration for cancer or autoimmune therapies as taught herein are set forth in Table 1. In a specific embodiment, the PI3K inhibitor used as the therapeutic agent is TGR1202. TGR-1202 (previously known as RP5264) is a highly selective inhibitor for the δ isoform of phosphatidylinositol 3-kinase (PI3K), referred to as PI3Kδ. It is well-tolerated and has greatly reduced hepatoxicity compared to other, less selective PI3K inhibitors and has nanomolar potency.

A phosphatidylinositol 3-kinase (PI3K) inhibitor is a class of drug that inhibits one or more of the four isoforms (α, β, γ, or δ) of the phosphoinositide 3-kinase enzymes. These enzymes are a part of the PI3K-AKT-mTOR signaling pathway, which regulates the cell cycle and is important to the survival of cancer cells. PI3K is constitutively active in some hematologic cancers such as chronic lymphocytic leukemia (CLL). This constitutive activity allows the cells to evade apoptosis. The δ isoform, PI3Kδ, is predominantly expressed in cells of hematologic origin and is largely confined to lymphocytes.

TGR-1202 acts by interfering with the PI3K-AKT-mTOR pathway (inhibiting AKT phosphorylation) to enable cancer cells to undergo apoptosis. TGR-1202 targets PI3Kδ. It has been shown effective in vitro against CLL and is being tested in studies for other hematologic cancers, for example, B cell lymphomas.

The chemical structure of TGR-1202 is given below.

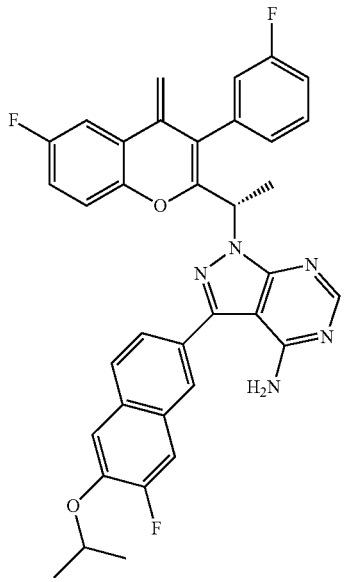

TGR-1202

Compounds according to the generic structure of Formula IV below are also PI3Kδ inhibitors that may be used in accord with the embodiments herein:

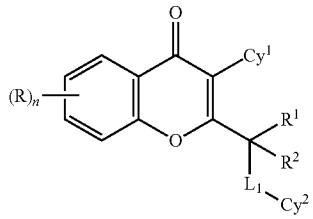

Formula IV or a tautomer thereof, N-oxide thereof, pharmaceutically acceptable ester thereof, prodrug thereof, or pharmaceutically acceptable salt thereof, wherein each occurrence of R is independently selected from hydrogen, halogen, —OR$^a$, CN, substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{3-8}$ cycloalkyl, and substituted or unsubstituted heterocyclic group;

R$^1$ and R$^2$ may be the same or different and are independently selected from hydrogen, halogen, and substituted or unsubstituted $C_{1-6}$ alkyl, or both R$^1$ and R$^2$ directly bound to a common atom, may be joined to form an oxo group (=O) or a substituted or unsubstituted saturated or unsaturated 3-10 member ring (including the carbon atom to which R$^1$ and R$^2$ are bound), which may optionally include one or more heteroatoms which may be the same or different and are selected from O, NR$^a$ and S;

Cy$^1$ is a monocyclic group selected from substituted or unsubstituted cycloalkyl, substituted or unsubstituted heterocyclic group, substituted or unsubstituted aryl and substituted or unsubstituted heteroaryl;

Cy$^2$ is selected from a substituted or unsubstituted heterocyclic group, substituted or unsubstituted aryl and substituted or unsubstituted heteroaryl;

L$_1$ is absent or selected from —(CR$^a$R$^b$)$_q$—, —O—, —S(=O)$_q$—, —NR$^a$— or —C(=Y)—, each occurrence of R$^a$ and R$^b$ may be the same or different and are independently selected from hydrogen, halogen, hydroxy, cyano, substituted or unsubstituted $(C_{1-6})$alkyl, —NR$^c$R$^d$ (wherein R$^c$ and R$^d$ are independently hydrogen, halogen, hydroxy, cyano, substituted or unsubstituted $(C_{1-6})$alkyl, and $(C_{1-6})$alkoxy) and —OR$^c$ (wherein R$^c$ is substituted or unsubstituted $(C_{1-6})$alkyl) or when R$^a$ and R$^b$ are directly bound to a common atom, they may be joined to form an oxo group (=O) or form a substituted or unsubstituted saturated or unsaturated 3-10 member ring (including the common atom to which R$^a$ and R$^b$ are directly bound), which may optionally include one or more heteroatoms which may be the same or different and are selected from 0, NR$^d$ (wherein R$^d$ is hydrogen or substituted or unsubstituted $(C_{1-6})$alkyl) or S;

Y is selected from O, S, and NR$^a$; n is an integer from 1 to 4; and q is 0, 1 or 2; are expected to have the same activity and are contemplated as part of the invention.

Certain preferred compounds are those according to Formula V:

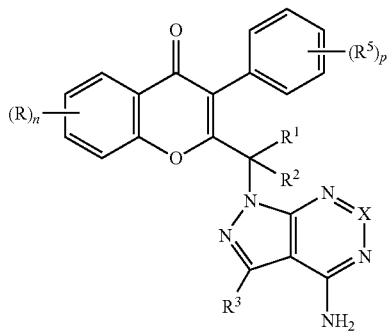

Formula V or a pharmaceutically acceptable salt thereof, wherein each occurrence of R is independently selected from hydrogen, halogen, —OR$^a$, CN, substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{3-8}$ cycloalkyl, and substituted or unsubstituted heterocyclic group;

R$^1$ and R$^2$ may be the same or different and are independently selected from hydrogen, halogen, and substituted or unsubstituted $C_{1-6}$ alkyl, or both R$^1$ and R$^2$ directly bound to a common atom, may be joined to form an oxo group (=O) or a substituted or unsubstituted saturated or unsaturated 3-10 member ring (including the carbon atom to which R$^1$ and R$^2$ are bound), which may optionally include one or more heteroatoms which may be the same or different and are selected from O, NR$^a$ and S; each occurrence of X is independently selected from CR$^3$ or N; and each occurrence of R$^3$ is independently selected from hydrogen, hydroxy, halogen, carboxyl, cyano, nitro, substituted or unsubstituted alkyl, substituted or unsubstituted alkoxy, substituted or unsubstituted alkenyl, substituted or unsubstituted alkynyl, substituted or unsubstituted aryl, substituted or unsubstituted arylalkyl, substituted or unsubstituted cycloalkyl, substituted or unsubstituted cycloalkylalkyl, substituted or unsubstituted cycloalkenylalkyl substituted or unsubstituted cycloalkenyl, substituted or unsubstituted heteroaryl, substituted or unsubstituted heteroarylalkyl, substituted or unsubstituted heterocyclic ring, substituted heterocyclylalkyl ring, substituted or unsubstituted guanidine, —COOR$^x$, —C(O)R$^x$, —C(S)R$^x$, —C(O)NR$^x$R$^y$, —C(O)ONR$^x$R$^y$, —NR$^y$R$^z$, —NR$^x$CONR$^y$R$^z$, —N(R$^x$)SOR$^y$, —N(R$^x$)SO$_2$R$^y$, —(=N—N(R$^x$)R$^x$), —NR$^x$C(O)OR$^y$, —NR$^x$R$^y$, —NR$^x$C(O)R$^y$—, —NR$^x$C(S)R$^y$—NR$^x$C(S)NR$^y$R$^z$, —SONR$^x$R$^y$—, —SO$_2$NR$^x$R$^y$—, —OR$^x$, —OR$^x$C(O)NR$^y$R$^z$, —OR$^x$C(O) OR$^y$—, —OC(O)R$^x$, —OC(O)NR$^x$R$^y$, —R$^x$NR$^y$C(O)R$^z$, R$^x$OR$^y$, —R$^x$C(O)OR$^y$, —R$^x$C(O)NR$^y$R$^z$, —R$^x$C(O)R$^x$, —R$^x$OC(O)R$^y$, —SR$^x$, —SOR$^x$, —SO$_2$R$^x$, and —ONO$_2$, wherein R$^x$, R$^y$ and R$^z$ in each of the above groups can be hydrogen, substituted or unsubstituted alkyl, substituted or unsubstituted alkoxy, substituted or unsubstituted alkenyl, substituted or unsubstituted alkynyl, substituted or unsubstituted aryl, substituted or unsubstituted arylalkyl, substituted or unsubstituted cycloalkyl, substituted or unsubstituted cycloalkylalkyl, substituted or unsubstituted cycloalkenyl, substituted or unsubstituted heteroaryl, substituted or unsubstituted heteroarylalkyl, substituted or unsubstituted heterocyclic ring, substituted or unsubstituted heterocyclylalkyl ring, or substituted or unsubstituted amino, or any two of R$^x$, R$^y$ and R$^z$ may be joined to form a substituted or unsubstituted saturated or unsaturated 3-10 membered ring, which may optionally include heteroatoms which may be the same or different and are selected from O, NR$^X$ (e.g., R$^x$ can be hydrogen or substituted or unsubstituted alkyl) or S; each occurrence of R$^5$ is hydrogen, C$_{1-6}$ alkyl or halogen; n is 0, 1, 2, 3 or 4; and p is 0, 1, 2, 3, 4 or 5.

In another embodiment, PI3K inhibitors include those according to Formula IV or a tautomer thereof, N-oxide thereof, pharmaceutically acceptable ester thereof, prodrug thereof, or pharmaceutically acceptable salt thereof, wherein each occurrence of R is independently selected from hydrogen, halogen, —OR$^f$ (wherein R$^f$ is substituted or unsubstituted (C$_{1-6}$)alkyl), CN, substituted or unsubstituted C$_{.1-6}$ alkyl, substituted or unsubstituted C$_{2-6}$ alkenyl, substituted or unsubstituted C$_{2-6}$ alkynyl, substituted or unsubstituted C$_{3-8}$ cycloalkyl, and substituted or unsubstituted heterocyclic group;

R$^1$ and R$^2$ may be the same or different and are independently selected from hydrogen, halogen, and substituted or unsubstituted C$_{1-6}$ alkyl, or both R$^1$ and R$^2$ directly bound to a common atom, may be joined to form a substituted or unsubstituted saturated or unsaturated 3-10 member ring (including the carbon atom to which R$^1$ and R$^2$ are bound), which may optionally include one or more heteroatoms which may be the same or different and are selected from O, NR$^a$ and S;

Cy$^1$ is a monocyclic group selected from substituted or unsubstituted cycloalkyl, substituted or unsubstituted heterocyclic group, substituted or unsubstituted aryl and substituted or unsubstituted heteroaryl;

Cy$^2$ is selected from a substituted or unsubstituted heterocyclic group, substituted or unsubstituted aryl and substituted or unsubstituted heteroaryl;

L$^1$ is selected from —S(=O)$_q$— and —NR$^a$—; each occurrence of R$^a$ is selected from hydrogen, halogen, hydroxy, cyano, substituted or unsubstituted (C$_{1-6}$)alkyl, —NR$^c$R$^d$ (wherein R$^c$ and R$^d$ are independently hydrogen, halogen, hydroxy, cyano, substituted or unsubstituted (C$_{1-6}$)alkyl, and (C$_{1-6}$)alkoxy) and —OR$^c$ (wherein R$^c$ is substituted or unsubstituted (C$_{1-6}$)alkyl);

n is an integer from 1 to 4; and q is 0, 1 or 2.

CK-1 Inhibitors

Few if any CK-1 inhibitors have been tested in humans. Certain compounds currently known as PI3K inhibitors have been discovered to possess CK-1 inhibitory activity as well, i.e., dual PI3K/CK-1 inhibitors. Thus, given the discovery that these PI3K inhibitor compounds possess CK-1 inhibition, they in actuality represent a new class of CK-1 inhibitors that would be suitable for human trials. Based on x-ray crystal structure analysis, TGR-1202 is structurally related to the known CK-1ε inhibitor PF4800567. In silico docking studies targeting the ATP binding pocket of CK1ε showed that TGR-1202 possessed high docking scores in binding modes highly consistent with PF4800567. Equipped with this information, compounds having structural similarity to certain portions of the TG1-1202 compound allow for the identification of CK-1 inhibitors from known compounds, or the design of new compounds having CK-1 activity.

The compounds of Formulas IV and V above represent examples of this new class of CK-1 inhibitors. Also, compounds described in WO2015/001491, incorporated by reference, are compounds belonging to this new class of CK-1 inhibitors. In addition, compounds according to Formulas I or Formula II with the defined R groups below represent embodiments of this new class of CK-1 inhibitors:

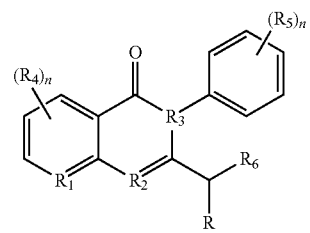

Formula I

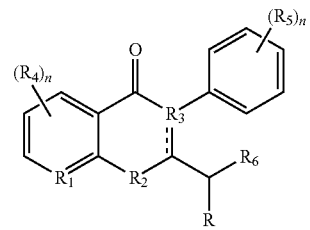

Formula II wherein

R is H or any one of groups A-G:

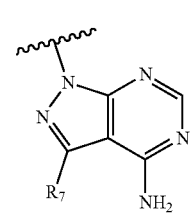

A

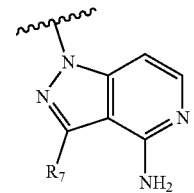

B

-continued

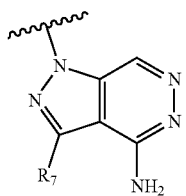

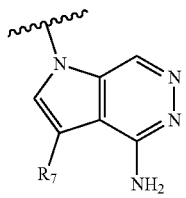

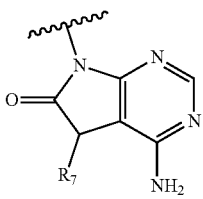

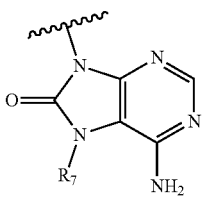

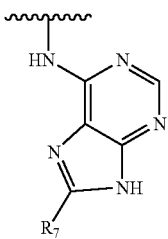

and wherein
═══ represents a single or double bond;
$R_1$ is CH, substituted C or N;
$R_2$
  in the compound of Formula I is CH, substituted C or N;
  in the compound of Formula II is O, $CH_2$, substituted C, NH or substituted N;
$R_3$
  in the compound of Formula I is CH, substituted C or N;
  in the compound of Formula II is
    CH, substituted C or N when ═══ represents a single bond; or
    C when ═══ represents a double bond;
each $R_4$ is independently substituted alkyl, unsubstituted alkyl, substituted alkenyl, unsubstituted alkenyl, substituted alkynyl, unsubstituted alkynyl, or halogen;
each $R_5$ is independently substituted alkyl, unsubstituted alkyl, substituted alkenyl, unsubstituted alkenyl, substituted alkynyl, unsubstituted alkynyl, or halogen;
$R_6$ is H, Me or Me substituted with halogen;
$R_7$ is H or a group selected from any one of groups J, K and H;

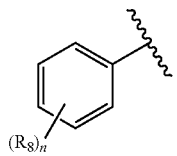

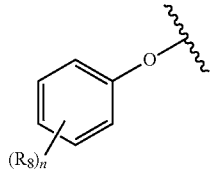

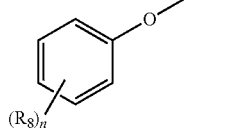

and
each $R_8$ is independently substituted alkyl, unsubstituted alkyl, substituted O-alkyl, unsubstituted O-alkyl or halogen;
n,
  for $R_4$ and when $R_1$ is not N, is 0, 1, 2, 3 or 4;
  for $R_4$ and when $R_1$ is N, is 0, 1, 2 or 3;
  for $R_5$ is 0, 1, 2, 3, 4 or 5;
  for $R_8$ is 0, 1, 2, 3, 4 or 5;

In certain embodiments, compounds of formula VI exclude those wherein at the same time R is group A, $R_1$ is CH, $R_3$ is N and $R_7$ is J.

In other embodiments, compounds of formula VII exclude those wherein at the same time R is group A, $R_1$ is CH, $R_2$ is O, $R_3$ is C, ═══ represents a double bond, and $R_7$ is J.

In other certain embodiments, $R_7$ is not H when R is group G.

In other embodiments, compounds include those of Formulas VI and VII with the provisos that
  compounds of formula VI wherein at the same time R is group A, $R_1$ is CH, $R_3$ is N and $R_7$ is J, are excluded;
  compounds of formula VII wherein at the same time R is group A, $R_1$ is CH, $R_2$ is O, $R_3$ is C, ═══ represents a double bond, and $R_7$ is J, are excluded;
  $R_7$ is not H when R is group G.

In specific embodiments, the following apply to immediately preceding definitions of Formulas I and II:
$R_1$ is N;
$R_2$ is not O;
$R_3$ is not N;
$R_4$ is halogen and n for $R_4$ is 1 or 2;
$R_4$ is F and n for $R_4$ is 1 or 2;
$R_4$ is F, n for $R_4$ is 1, and $R_4$ is located at position 5 of the quinazolin-4-one ring to which it is attached;
n for $R_5$ is 0;
$R_6$ is Me; R is not group A;
R is group A;
$R_7$ is J; $R_7$ is not J;
n for $R_8$ is 2, one $R_8$ is isopropyl or O-isopropyl, and the other $R_8$ is halogen, preferably F; and/or R<sub>7</sub> is one of the following:

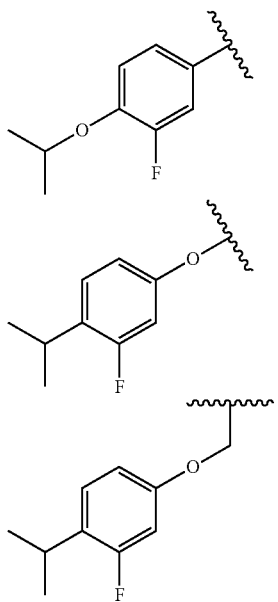

Compounds according to formulas I and II may be prepared by adapting the techniques of PCT publication Nos. WO2015001491, WO2008/127226, WO2009/088986, WO 2011/055215 and WO 2012/151525, which are incorporated herein by reference. Those skilled in the art would be able to modify the preparation schemes of these references to produce the such compounds.

Derivatives

According to certain embodiments, as used herein, derivatives of the c-Myc reducing agents and adjunct c-Myc inhibitors as discussed herein and as set forth in the accompanying tables include salts, esters, enol ethers, enol esters, acetals, ketals, orthoesters, hemiacetals, hemiketals, solvates, hydrates, metabolites or prodrugs thereof. Such derivatives may be readily prepared by those of skill in this art using known methods for such derivatization. The compounds produced may be administered to animals or humans without substantial toxic effects and either are pharmaceutically active or are prodrugs. Pharmaceutically acceptable salts include, but are not limited to, amine salts, such as but not limited to N,N'-dibenzylethylenediamine, chloroprocaine, choline, ammonia, diethanolamine and other hydroxyalkylamines, ethylenediamine, N-methylglucamine, procaine, N-benzylphenethylamine, 1-para-chlorobenzyl-2-pyrrolidin-1'-ylmethyl-benzimidazole, diethylamine and other alkylamines, piperazine and tris(hydroxymethyl)aminomethane; alkali metal salts, such as but not limited to lithium, potassium and sodium; alkali earth metal salts, such as but not limited to barium, calcium and magnesium; transition metal salts, such as but not limited to zinc; and other metal salts, such as but not limited to sodium hydrogen phosphate and disodium phosphate; and also including, but not limited to, salts of mineral acids, such as but not limited to hydrochlorides and sulfates; and salts of organic acids, such as but not limited to acetates, lactates, malates, tartrates, citrates, ascorbates, succinates, butyrates, valerates and fumarates. Pharmaceutically acceptable esters include, but are not limited to, alkyl, alkenyl, alkynyl, alk(en)(yn)yl, aryl, aralkyl, and cycloalkyl esters of acidic groups, including, but not limited to, carboxylic acids, phosphoric acids, phosphinic acids, sulfonic acids, sulfinic acids and boronic acids. Pharmaceutically acceptable enol ethers include, but are not limited to, derivatives of formula C=C(OR) where R is hydrogen, alkyl, alkenyl, alkynyl, alk(en)(yn)yl, aryl, aralkyl, or cycloalkyl. Pharmaceutically acceptable enol esters include, but are not limited to, derivatives of formula C=C(OC(O)R) where R is hydrogen, alkyl, alkenyl, alkynyl, aryl, aralkyl, or cycloalkyl. Pharmaceutically acceptable solvates and hydrates are complexes of a compound with one or more solvent or water molecules, or 1 to about 100, or 1 to about 10, or one to about 2, 3 or 4, solvent or water molecules.

According to further embodiments, derivatives may include, but are not limited to, specific substitutions of reactive constituents on or emanating from an example agent may include, but are not limited to, one or more of the following: a hydrogen, hydroxy, halo, haloalkyl, thiocarbonyl, alkoxy, alkenoxy, alkylaryloxy, aryloxy, arylalkyloxy, cyano, nitro, imino, alkylamino, aminoalkyl, aminodialkyl, thio, sulfhydryl, thioalkyl, alkylthio, sulfonyl, C1-C6 straight or branched chain alkyl, C2-C6 straight or branched chain alkenyl or alkynyl, aryl, aralkyl, heteroaryl, carbocycle, or heterocycle group or moiety, or CO2 R7 where R7 is hydrogen or C1-C9 straight or branched chain alkyl or C2-C9 straight or branched chain alkenyl group or moiety.

It is to be understood that the compounds provided herein may contain chiral centers. Such chiral centers may be of either the (R) or (S) configuration, or may be a mixture thereof. Thus, the compounds provided herein may be enantiomerically pure, or be stereoisomeric or diastereomeric mixtures. It is to be understood that the chiral centers of the compounds provided herein may undergo epimerization in vivo. As such, one of skill in the art will recognize that administration of a compound in its (R) form is equivalent, for compounds that undergo epimerization in vivo, to administration of the compound in its (S) form.

As used herein, alkyl refers to an unbranched or branched hydrocarbon chain. An alkyl group may be unsubstituted or substituted with one or more heteroatoms.

As used herein, alkenyl refers to an unbranched or branched hydrocarbon chain comprising one or more double bonds. The double bond of an alkenyl group may be unconjugated or conjugated to another unsaturated group. An alkenyl group may be unsubstituted or substituted with one or more heteroatoms.

As used herein, alkynyl refers to an unbranched or branched hydrocarbon chain comprising one of more triple bonds therein. The triple bond of an alkynyl group may be unconjugated or conjugated to another unsaturated group. An alkynyl group may be unsubstituted or substituted with one or more heteroatoms.

As used herein, alk(en)(yn)yl refers to an unbranched or branched hydrocarbon group comprising at least one double bond and at least one triple bond. The double bond or triple bond of an alk(en)(yn)yl group may be unconjugated or conjugated to another unsaturated group. An alk(en)(yn)yl group may be unsubstituted or substituted with one or more heteroatoms.

Exemplary alkyl, alkenyl, alkynyl, and alk(en)(yn)yl groups herein include, but are not limited to, methyl, ethyl, propyl, isopropyl, isobutyl, n-butyl, sec-butyl, tert-butyl, isopentyl, neopentyl, tert-pentyl, isohexyl, allyl (propenyl) and propargyl (propynyl).

As used herein, "aryl" refers to aromatic monocyclic or multicyclic groups containing from 6 to 19 carbon atoms. Aryl groups include, but are not limited to groups such as unsubstituted or substituted fluorenyl, unsubstituted or substituted phenyl, and unsubstituted or substituted naphthyl.

As used herein, "heteroaryl" refers to a monocyclic or multicyclic aromatic ring system, in certain embodiments, of about 5 to about 15 members where one or more, in one embodiment 1 to 3, of the atoms in the ring system is a heteroatom, that is, an element other than carbon, including but not limited to, nitrogen, oxygen or sulfur. The heteroaryl group may be optionally fused to a benzene ring. Heteroaryl groups include, but are not limited to, furyl, imidazolyl, pyrimidinyl, tetrazolyl, thienyl, pyridyl, pyrrolyl, thiazolyl, isothiazolyl, oxazolyl, isoxazolyl, triazolyl, quinolinyl or isoquinolinyl.

As used herein, "halo," "halogen," or "halide" refers to F, Cl, Br or I.

As used herein, base refers to any compound that accepts protons in water or solvent. Thus, exemplary bases include, but are not limited to, alkali metal hydroxides and alkali metal alkoxides (i.e., MOR, wherein M is an alkali metal such as but not limited to potassium, lithium, or sodium and R is hydrogen, alkyl, alkenyl, alkynyl, or alk(en)(yn)yl) such as but not limited to potassium hydroxide, potassium tert-butoxide, potassium tert-pentoxide, sodium hydroxide, sodium tert-butoxide, lithium hydroxide, etc.); other hydroxides such as but not limited to magnesium hydroxide (Mg(OH)2), calcium hydroxide (Ca(OH)2), or barium hydroxide (Ba(OH)2); alkali metal hydrides (i.e., MH, wherein M is as defined above) such as but not limited to sodium hydride, potassium hydride, or lithium hydride; carbonates such as but not limited to potassium carbonate (K2CO3), sodium carbonate (Na2CO3), potassium bicarbonate (KHCO3), or sodium bicarbonate (NaHCO3); alkyl ammonium hydroxides, alkenyl ammonium hydroxides, alkynyl ammonium hydroxides, or alk(en)(yn)yl ammonium hydroxides such as but not limited to n-tetrabutyl ammonium hydroxide (TBAH); amines such as ammonia, diethylamine, 2,2,6,6-tetramethyl piperidine (HTMP), tertiary amines (such as but not limited to dimethylethyl amine, diisopropylethylamine, trimethylamine, triethylamine, tributylamine, N-methylmorpholine, N-methylpyrrolidine, 1,8-diazabicyclo[5.4.0]-7-undecene (DBU), 1,5-diazabicyclo[4.3.0]-5-nonene (DBN), or tetramethylenediamine (TMEDA)), aromatic amines (such as but not limited to pyridine, collidine, lutidine, picoline, quinoline, or N,N-dimethylaniline); alkali metal amides such as but not limited to lithium amide, lithium dimethylamide, lithium diisopropylamide (LDA), lithium tetramethylpiperidide (LiTMP), or alkali metal hexamethyldisilazanes (such as but not limited to potassium hexamethyldisilazane, (KHMDS), sodium hexamethyldisilazane (NaHMDS), or lithium hexamethyldisilazane (LiHMDS)); alkyl lithiums, alkenyl lithiums, alkynyl lithiums, or alk(en)(yn)yl lithiums such as but not limited to n-butyl lithium sec-butyllithium, isopropyllithium; alkyl magnesium halides, alkenyl magnesium halides, alkynyl magnesium halides, or alk(en)(yn)yl magnesium halides such as but not limited to methyl magnesium bromide.

As used herein, solvent refers to any liquid that completely or partially dissolves a solid, liquid, or gaseous solute, resulting in a solution such as but not limited to hexane, benzene, toluene, diethyl ether, chloroform, ethyl acetate, dichloromethane, carbon tetrachloride, 1,4-dioxane, tetrahydrofuran, glyme, diglyme, acetone, acetonitrile, dimethylformamide, dimethyl sulfoxide, dimethylacetamide, or N-methyl-2-pyrrolidone.

As used herein, dehydrating agent refers to any compound that promotes the formation of carboxamides from carboxylic acids, such as but not limited to thionyl chloride, sulfuryl chloride, a carbodiimide, an anhydride or a mixed anhydride, a phenol (such as but not limited to nitrophenol, pentafluorophenol, or phenol), or a compound of Formula (A):

wherein each of X and Y is independently an unsubstituted or substituted heteroaryl group (such as but not limited to imidazolyl, benzimidazolyl, or benzotriazolyl). Examples of dehydrating agents further include, but are not limited to, benzotriazole-1-yl-oxy-tris-(dimethylamino)-phosphonium hexafluorophosphate (BOP), N,N'-carbonyldiimidazole (CDI), 3-(diethoxyphosphoryloxy)-1,2,3-benzotriazin-4 (3H)-one (DEPBT), 1-ethyl-3-(3-dimethyllaminopropyl) carbodiimide (EDC), 2-(7-aza-1H-benzotriazole-1-yl)-1,1,3,3-tetramethyluronium hexafluorophosphate (HATU), 2-(1H-benzotriazole-1-yl)-1,1,3,3-tetramethyluronium hexafluorophosphate (HBTU), 1-hydroxybenzotriazole (HOBt), benzotriazole-1-yl-oxy-tris-pyrrolidino-phosphonium hexafluorophosphate (PyBOP), 2-(1H-benzotriazole-1-yl)-1,1,3,3-tetramethyluronium tetrafluoroborate (TBTU). O-(3,4-dihydro-4-oxo-1,2,3-benzotriazine-3-yl)-N,N,N,N-tetra methyluronium tetrafluoroborate (TDBTU), 3-(diethyloxyphosphoryloxy)-1,2,3-benzotriazin-4(3H)-one (DEPBT), dicyclohexylcarbodiimide (DCC), N,N'-diisopropylcarbodiimide (DIC), or 1-hydroxy-7-azabenzotriazole (HOAt).

As used herein, acid refers to any compound that contains hydrogen and dissociates in water or solvent to produce positive hydrogen ions, as well as Lewis acids, including but not limited to hydrochloric acid, sulfuric acid, phosphoric acid, acetic acid, trihaloacetic acids (such as but not limited to trifluoroacetic acid or trichloroacetic acid), hydrogen bromide, maleic acid, sulfonic acids (such as but not limited to toluenesulfonic acids or camphorsulfonic acids), propionic acids (such as but not limited to (R)-chloropropionic acid), phthalamic acids (such as but not limited to N—[(R)-1-(1-naphthyl)ethyl]phthalamic acid), tartaric acids (such as but not limited to L-tartaric acid or dibenzyl-L-tartaric acid), lactic acids, camphoric acids, aspartic acids, or citronellic acids.

It is to be understood that reactants, compounds, solvents, acids, bases, catalysts, agents, reactive groups, or the like may be added individually, simultaneously, separately, and in any order. Furthermore, it is to be understood that reactants, compounds, acids, bases, catalysts, agents, reactive groups, or the like may be pre-dissolved in solution and added as a solution (including, but not limited to, aqueous solutions). In addition, it is to be understood that reactants, compounds, solvents, acids, bases, catalysts, agents, reactive groups, or the like may be in any molar ratio.

It is to be understood that reactants, compounds, solvents, acids, bases, catalysts, agents, reactive groups, or the like may be formed in situ.

Enantiomers/Tautomers

Agents also include where appropriate all enantiomers and tautomers of the enumerated agents. The skilled artisan will recognise compounds that possess an optical properties (one or more chiral carbon atoms) or tautomeric characteristics. The corresponding enantiomers and/or tautomers may be isolated/prepared by methods known in the art.

Stereo and Geometric Isomers

Enumerated agents may exist as stereoisomers and/or geometric isomers—e.g. they may possess one or more asymmetric and/or geometric centres and so may exist in two or more stereoisomeric and/or geometric forms. Contemplated herein is the use of all the individual stereoisomers and geometric isomers of those inhibitor agents, and mixtures thereof. The terms used in the claims encompass these forms, provided said forms retain the appropriate functional activity (though not necessarily to the same degree).

Enumerated agents also include all suitable isotopic variations of the example agent or pharmaceutically acceptable salts thereof. An isotopic variation of an agent or a pharmaceutically acceptable salt thereof is defined as one in which at least one atom is replaced by an atom having the same atomic number but an atomic mass different from the atomic mass usually found in nature. Examples of isotopes that can be incorporated into the agent and pharmaceutically acceptable salts thereof include isotopes of hydrogen, carbon, nitrogen, oxygen, phosphorus, sulphur, fluorine and chlorine such as 2H, 3H, 13C, 14C, 15N, 17O, 18O, 31P, 32P, 35S, 18F and 36Cl, respectively. Certain isotopic variations of the agent and pharmaceutically acceptable salts thereof, for example, those in which a radioactive isotope such as 3H or 14C is incorporated, are useful in drug and/or substrate tissue distribution studies. Tritiated, i.e., 3H, and carbon-14, i.e., 14C, isotopes are particularly preferred for their ease of preparation and detectability. Further, substitution with isotopes such as deuterium, i.e., 2H, may afford certain therapeutic advantages resulting from greater metabolic stability, for example, increased in vivo half-life or reduced dosage requirements and hence may be preferred in some circumstances. Isotopic variations of the example agents and pharmaceutically acceptable salts thereof of this disclosure can generally be prepared by conventional procedures using appropriate isotopic variations of suitable reagents.

Solvates

Enumerated agents also include solvate forms of the example agents. The terms used in the claims encompass these forms.

Polymorphs

Enumerated agents also include their various crystalline forms, polymorphic forms and (an)hydrous forms. It is well-established within the pharmaceutical industry that chemical compounds may be isolated in any of such forms by slightly varying the method of purification and or isolation form the solvents used in the synthetic preparation of such compounds.

Prodrugs

Embodiments of the disclosure further include enumerated agents in prodrug form. Such prodrugs are generally compounds wherein one or more appropriate groups have been modified such that the modification may be reversed upon administration to a human or mammalian subject. Such reversion is usually performed by an enzyme naturally present in such subject, though it is possible for a second agent to be administered together with such a prodrug in order to perform the reversion in vivo. Examples of such modifications include ester (for example, any of those described above), wherein the reversion may be carried out be an esterase etc. Other such systems will be well known to those skilled in the art.

Metabolites

Also falling within the scope of this invention are the in vivo metabolic products of enumerated agents. A "metabolite" is a pharmacologically active product produced through metabolism in the body of a specified compound or salt thereof. Such products can result, for example, from the oxidation, reduction, hydrolysis, amidation, deamidation, esterification, deesterification, enzymatic cleavage, and the like, of the administered compound. Accordingly, the invention includes metabolites of example agents, including compounds produced by a process comprising contacting a compound of this invention with a mammal for a period of time sufficient to yield a metabolic product thereof.

Metabolites are identified, for example, by preparing a radiolabelled (e.g., $^{14}C$ or $^{3}H$) isotope of a compound of the invention, administering it parenterally in a detectable dose (e.g., greater than about 0.5 mg/kg) to an animal such as rat, mouse, guinea pig, monkey, or to a human, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g., by MS, LC/MS or NMR analysis. In general, analysis of metabolites is done in the same way as conventional drug metabolism studies well known to those skilled in the art. The metabolites, so long as they are not otherwise found in vivo, are useful in diagnostic assays for therapeutic dosing of the compounds of the invention.

Interfering Molecules

Expression of PI3K or CK-1 can be inhibited by a number of means including silencing via antisense, miRNA, shRNA, or siRNA, for example, directed to a portion of the sequence described at the genbank accession numbers provided herein. In one embodiment, an inhibitor of PI3K or CK-1 or proteasomes comprises an interfering molecule, and wherein the interfering molecule comprises a member selected from the group consisting of a phosphothioate morpholino oligomer (PMO), miRNA, siRNA, methylated siRNA, treated siRNAs, shRNA, antisense RNA, a dicer-substrate 27-mer duplex, and combinations thereof.

siRNA molecules can be prepared against a portion of a nucleotide sequence encoding PI3K or CK-1, according to the techniques provided in U.S patent publication 2006/0110440, incorporated by reference herein, and used as therapeutic compounds. shRNA constructs are typically made from one of three possible methods; (i) annealed complementary oligonucleotides, (ii) promoter based PCR or (iii) primer extension. See Design and cloning strategies for constructing shRNA expression vectors, Glen J. McIntyre, Gregory C. Fanning, BMC Biotechnology 2006, 6:1 (5 Jan. 2006).

For background information on the preparation of miRNA molecules, see e.g. U.S. patent publications 2011/0020816, 2007/0099196; 2007/0099193; 2007/0009915; 2006/0130176; 2005/0277139; 2005/0075492; and 2004/0053411, the disclosures of which are hereby incorporated by reference herein. See also U.S. Pat. Nos. 7,056,704 and 7,078,196 (preparation of miRNA molecules). Synthetic miRNAs are described in Vatolin et al., 2006 J Mol Biol 358, 983-6 and Tsuda et al., 2005 Int J Oncol 27, 1299-306. See also patent documents WO2011/127202 for further examples of interfering molecules for targeting CK-1, for example.

Administration of Enumerated Therapeutic Agents

Certain embodiments involve administering at least one c-Myc reducing agent or combination of c-Myc reducing agents and adjunct c-Myc inhibitors to treat cancer, such as c-Myc overexpressing cancers including hematologic cancers so as to deliver the agent or agents to a subject in need. Other embodiments involve administration of a combination of at least one c-Myc reducing agent and at least one adjunct c-Myc inhibitor, and optionally at least one adjunct cancer therapeutic agent. In a specific embodiment, the adjunct c-Myc inhibitor includes, but is not limited to, PI3K-AKT-mTOR signaling pathway inhibitor, proteasome inhibitor, or CK-1 inhibitor, including analogs or derivatives thereof, or pharmaceutically acceptable salts thereof. The PI3K-AKT-mTOR signaling pathway inhibitor is a dual PI3K/CK-1 inhibitor. In more specific embodiments, administration of a c-Myc reducing agent alone, or co-administration of a c-Myc reducing agent and an adjunct c-Myc inhibitor, may be provided as a lead-in therapy in a manner to reduce or initiate reduction of c-Myc prior to administration of the adjunct cancer therapeutic agent.

Modes of administering include, but are not limited to oral administration, parenteral administration such as intravenous, subcutaneous, intramuscular or intraperitoneal injections, rectal administration by way of suppositories, transdermal administration, intraocular administration or administration by any route or method that delivers a therapeutically effective amount of the drug or composition to the cells or tissue to which it is targeted. Alternatively, routine experimentation will determine other acceptable routes of administration.

Typically, agents are administered to a subject in an amount effective to achieve a desired therapeutic effect. The therapeutically effective amount will vary depending on the compound, the disease and its severity and the age, weight, etc., of the subject to be treated. In the context of treating cancer, a therapeutically effective amount refers to the amount of a therapy that is sufficient to result in the prevention of the development, recurrence, or onset of cancer and one or more symptoms thereof, to enhance or improve the prophylactic effect(s) of another therapy, reduce the severity, the duration of cancer, ameliorate one or more symptoms of cancer, prevent the advancement of cancer, cause regression of cancer, and/or enhance or improve the therapeutic effect(s) of another therapy. In an embodiment of the invention, the amount of a therapy is effective to achieve one, two, three or more of the following results following the administration of one, two, three or more therapies: (1) a stabilization, reduction or elimination of the cancer stem cell population; (2) a stabilization, reduction or elimination in the cancer cell population; (3) a stabilization or reduction in the growth of a tumor or neoplasm; (4) an impairment in the formation of a tumor; (5) eradication, removal, or control of primary, regional and/or metastatic cancer; (6) a reduction in mortality; (7) an increase in disease-free, relapse-free, progression-free, and/or overall survival, duration, or rate; (8) an increase in the response rate, the durability of response, or number of patients who respond or are in remission; (9) a decrease in hospitalization rate; (10) a decrease in hospitalization lengths; (11) the size of the tumor is maintained and does not increase or increases by less than 10%, preferably less than 5%, preferably less than 4%, preferably less than 2%; (12) an increase in the number of patients in remission; (13) an increase in the length or duration of remission; (14) a decrease in the recurrence rate of cancer; (15) an increase in the time to recurrence of cancer; and (16) an amelioration of cancer-related symptoms and/or quality of life.

In a certain embodiment, a composition of this invention can be administered to a subject who has symptoms of or is diagnosed with a carcinoma. A composition of this invention can be administered prophylactically, i.e., before development of any symptom or manifestation of the disease, disorder or condition. Typically, in this case the subject will be at risk of developing the condition. Treating also may comprise treating a subject exhibiting symptoms of a certain disease, disorder or condition.

Co-administration of a combination of enumerated therapeutic agents, as described herein, may be accomplished by administering a mixed formulation comprising two or more agents (e.g., single composition). Alternatively, the two or more agents can be administered separately. The co-administration may be conducted by a first step of administering one of the therapeutic agents such as a c-Myc reducing agent, and a second step of administering a second agent such as an adjunct c-Myc inhibitor, wherein the first and the second administration steps may be conducted simultaneously or sequentially. In case of the sequential administration, the first step and the second step may be performed in any order, and separated by any suitable time interval (e.g., 1-60 seconds, 1-60 minutes, 1-24 hours, or 1-7 days). A first agent, such as a c-Myc reducing agent, and a second agent, such as an adjunct c-Myc inhibitor, may be administered in amounts that are therapeutically effective when combined, which amount may be determined by the skilled medical practitioner or medical researcher.

Adjunct Cancer Therapy

Disclosed herein is the discovery of new compounds that can reduce c-Myc in c-Myc overexpressing cells. The reduction of c-Myc expression makes the c-Myc overexpressing cells more susceptible to other adjunct cancer therapy protocols such as chemotherapy, surgery, radiotherapy, thermotherapy, cancer vaccines, immunotherapy, gene therapy and laser therapy. It is believed that the reduction of the c-Myc expression in the cancer cells makes the cells more susceptible to the cytotoxic effects of the proteasome inhibition. This same effect carries over to other cancer therapeutic agents. Accordingly, certain embodiments pertain methods that involve administering a c-Myc reducing agent, or a combination of a c-Myc reducing agent and an adjunct c-Myc inhibitor, with therapeutically effective amount of an adjunct cancer therapeutic agent to enhance treatment of c-Myc overexpressing cancer cells.

Pharmaceutical Formulations

Certain embodiments are directed to pharmaceutical formulations comprising a c-Myc reducing amount of a c-Myc reducing agent, or a combination of c-Myc reducing amount of a c-Myc reducing agent and an adjunct c-Myc inhibitor, wherein either the formulation of the c-Myc reducing agent alone or in combination with an adjunct c-Myc inhibitor, optionally further includes a therapeutically effective amount of an adjunct cancer therapeutic agent. Agents useful in therapeutic methods described herein may be provided in a formulation or composition acceptable for administration to a subject. Typically, agent(s) are provided with a pharmaceutically acceptable carrier. "Pharmaceutically acceptable carrier" is intended to include any and all solvents, binders, diluents, disintegrants, lubricants, dispersion media, coatings, antibacterial and antifungal agents, isotonic and absorption delaying agents, and the like, compatible with pharmaceutical administration. The use of such media and agents for pharmaceutically active substances is well known in the art. As long as any conventional media or agent is compatible with the active agent, such media can be used in the compositions of the invention and supplementary active agents or therapeutic agents can also be incorporated into the compositions. A pharmaceutical composition of the invention is formulated to be compatible with its intended route of administration.

Solutions or suspensions can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylene diamine tetra acetic acid; buffers such as acetates, citrates or phosphates and agents for the adjustment of tonicity such as sodium chloride or dextrose. pH can be adjusted with acids or bases, such as hydrochloric acid or sodium hydroxide.

Pharmaceutical compositions suitable for injectable use include sterile aqueous solutions (where the therapeutic agents are water soluble) or dispersions and sterile powders for the extemporaneous preparation of sterile injectable solutions or dispersion. For intravenous administration, suitable carriers include physiological saline, bacteriostatic water, Cremophor EL® (BASF, Parsippany, N.J.) or phosphate buffered saline (PBS). In all cases, the composition must be sterile and should be fluid to the extent that easy syringability exists. It should be stable under the conditions of manufacture and storage and should be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Further details on techniques for formulation and administration can be found in the latest edition of Remington: The Science and Practice of Pharmacy, 22nd ed. (Pharmaceutical Press, Philadelphia, Pa., 2012, which is incorporated herein by reference). After pharmaceutical compositions have been prepared, they can be placed in an appropriate container and labeled for treatment of an indicated condition. Such labeling would include amount, frequency, and method of administration.

As noted above, "therapeutically effective amount" refers to the amount of the subject compound that will elicit the biological or medical response of a tissue, system, or subject that is being sought by the researcher, veterinarian, medical doctor or other clinician. The term "therapeutically effective amount" includes that amount of a compound that, when administered, is sufficient to prevent development of, or alleviate to some extent, one or more of the signs or symptoms of the disorder or disease being treated. The therapeutically effective amount will vary depending on the compound, the disease and its severity and the age, weight, etc., of the subject to be treated. In the context of treating cancer, a therapeutically effective amount refers to the amount of a therapy that is sufficient to result in the prevention of the development, recurrence, or onset of cancer and one or more symptoms thereof, to enhance or improve the prophylactic effect(s) of another therapy, reduce the severity, the duration of cancer, ameliorate one or more symptoms of cancer, prevent the advancement of cancer, cause regression of cancer, and/or enhance or improve the therapeutic effect(s) of another therapy. In an embodiment of the invention, the amount of a therapy is effective to achieve one, two, three or more of the following results following the administration of one, two, three or more therapies: (1) a stabilization, reduction or elimination of the cancer stem cell population; (2) a stabilization, reduction or elimination in the cancer cell population; (3) a stabilization or reduction in the growth of a tumor or neoplasm; (4) an impairment in the formation of a tumor; (5) eradication, removal, or control of primary, regional and/or metastatic cancer; (6) a reduction in mortality; (7) an increase in disease-free, relapse-free, progression-free, and/or overall survival, duration, or rate; (8) an increase in the response rate, the durability of response, or number of patients who respond or are in remission; (9) a decrease in hospitalization rate; (10) a decrease in hospitalization lengths; (11) the size of the tumor is maintained and does not increase or increases by less than 10%, preferably less than 5%, preferably less than 4%, preferably less than 2%; (12) an increase in the number of patients in remission; (13) an increase in the length or duration of remission; (14) a decrease in the recurrence rate of cancer; (15) an increase in the time to recurrence of cancer; and (16) an amelioration of cancer-related symptoms and/or quality of life.

Therapeutic efficacy and toxicity, e.g., ED50 (the dose therapeutically effective in 50% of the population) and LD50 (the dose lethal to 50% of the population), can be determined by standard pharmaceutical procedures in cell cultures or experimental animals. The dose ratio of toxic to therapeutic effects is the therapeutic index, and it can be expressed as the ratio, LD50/ED50.

The exact dosage will be determined by the practitioner, in light of factors related to the subject that requires treatment. Dosage and administration are adjusted to provide sufficient levels of the active ingredient or to maintain the desired effect. Factors which can be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions can be administered every 3 to 4 days, every week, or once every two weeks depending on the half-life and clearance rate of the particular formulation.

Normal dosage amounts can vary from 0.1 to 100,000 micrograms, up to a total dose of about 1 g, depending upon the route of administration. An effective amount of the compound described above may range from about 0.1 mg/Kg to about 500 mg/Kg, alternatively from about 1 to about 50 mg/Kg. Effective doses will also vary depending on route of administration, as well as the possibility of co-usage with other agents. Clinicians can readily determine the therapeutically effective amount using techniques known in the art.

Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

Preferably, a therapeutic agent reduces expression of a target gene or the activity of a target polypeptide by at least about 10%, preferably about 50%, more preferably about 75%, 90%, or 100% relative to the absence of the reagent. The effectiveness of the mechanism chosen to decrease the level of expression of a target gene or the activity of a target polypeptide can be assessed such as by hybridization of nucleotide probes to target-specific mRNA, quantitative RT-PCR, immunologic detection of a target polypeptide, or measurement of target polypeptide activity.

In any of the embodiments described above, any of the pharmaceutical compositions of the invention can be administered in combination with other appropriate therapeutic agents. Selection of the appropriate agents for use in combination therapy can be made by one of ordinary skill in the art, according to conventional pharmaceutical principles.

The combination of therapeutic agents can act synergistically to effect the treatment of cancer. Using this approach, one may be able to achieve therapeutic efficacy with lower dosages of each agent, thus reducing the potential for adverse side effects. Any of the therapeutic methods described above can be applied to any subject in need of such therapy.

6. Examples

This invention is not limited to the particular processes, compositions, or methodologies described or exemplified, as these may vary. Although any methods and materials similar or equivalent to those described herein can be used in the practice or testing of embodiments of the present invention, the preferred methods, devices, and materials are described. It will, however, be evident that various modifications and changes may be made thereto without departing from the broader spirit and scope of the invention. Examples are provided below to facilitate a more complete understanding of the invention. The following examples illustrate the exemplary modes of making and practicing the invention, however, the scope of the invention is not limited to specific embodiments disclosed in these Examples, which are for purposes of illustration only. Those skilled in the art will recognize, or be able to ascertain, using no more than routine experimentation, numerous equivalents to the specific embodiments described herein. Such equivalents are considered to be within the scope of this invention.

Example 1. Materials and Methods

Cell Culture and Reagents

The cell lines were obtained from ATCC and grown in Iscove Modified Dulbecco Medium with 10% FCS. Fresh medium was added every 2 to 3 days, and the cells were kept at a cell concentration of 0.1 to $1 \times 10^6$/mL. For primary cells, the culture medium was RPMI. The reagents were purchased from Selleck, including carfilzomib, bortezomib, idelalisib/Cal-101. TGR-1202 was provided by TG Therapeutics.

Cytotoxicity Assay

Cytotoxicity was performed on cultured cells using Cell Titer Glo, as previously described [22]. Experiments were carried out in 96-well plates, with each treatment in triplicate. Samples were taken at typically 24 hours, 48 hours, and/or 72 hours after treatment, as indicated. Cytotoxicity was expressed by the decreasing percentage of live cells in each treatment relative to the untreated control from the same experiment, as a function of time. IC50 (half the maximal inhibitory concentration) for each cell line was calculated using the CalcuSyn Version 2.0 software (Biosoft).

Western Blot

Western blot was performed on whole protein extract from cultured cells under specified treatment conditions, most often for 24 hours. Western blotting was performed according to standard protocols, using the chemiluminescence detection system from Thermo Scientific. The primary antibodies were purchased from Cell Signaling Technology unless specified otherwise, and were against these proteins: 4EBP1, phos-4EBP1, S6K, phos-S6K, Bcl2, Bcl-xL, PARP, c-myc, B-catenin, P-4EBP1 (S65), P-4EBP1 (T70). Signals of beta-actin and GAPDH were used as loading control. Goat anti-rabbit or anti-mouse secondary antibodies were purchased from Santa Cruz Biotechnology.

CK1ε Kinase Activity Assay

The CK-1 assay was conducted according to the techniques disclosed in Anastassiadis et al, Nat Biotechnol; 29(11): 1039-1045. Briefly, specific kinase/substrate pairs along with required cofactors were prepared in reaction buffer; 20 mM Hepes pH 7.5, 10 mM MgCl2, 1 mM EGTA, 0.02% Brij35, 0.02 mg/ml BSA, 0.1 mM Na3VO4, 2 mM DTT, 1% DMSO (for specific details of individual kinase reaction components see Supplementary Table 2, Anastassiadis et al. 2011). Compounds were delivered into the reaction, followed ~20 minutes later by addition of a mixture of ATP (Sigma, St. Louis Mo.) and 33P ATP (Perkin Elmer, Waltham Mass.) to a final concentration of 10 µM. Reactions were carried out at room temperature for 120 min, followed by spotting of the reactions onto P81 ion exchange filter paper (Whatman Inc., Piscataway, N.J.). Unbound phosphate was removed by extensive washing of filters in 0.75% phosphoric acid. After subtraction of background derived from control reactions containing inactive enzyme, kinase activity data was expressed as the percent remaining kinase activity in test samples compared to vehicle (dimethyl sulfoxide) reactions. IC50 values and curve fits were obtained using Prism (GraphPad Software).

Substrate: Peptide substrate, [KRRRAL[pS]VASLPGL], 20 µM ATP 10 µM

Reaction: Substrate+[γ-33P]-ATP 33P-Substrate+ADP

Assay: radioisotope filtration binding assay (Reaction Biology).

Compounds were tested in 10-dose IC50 mode with 3-fold serial dilution starting at 100 µM Control Compound, D4476, was tested in 10-dose IC50 mode with 3-fold serial dilution starting at 20 µM Reactions were carried out at 10 µM ATP.

Example 2: CUX-03166 Reduces Viability of Lymphoma Cells

The lymphoma cell line LY10 was treated with CUX-03166 ('166 compound) for 24 hours, 48 hours and 72 hours. Cells were collected from the treatment group and the vehicle treated negative control. Viable cells were quantitated by the Cell-Titer Glo assay from Promega. Viable cells in the treated cells were expressed as a percentage of the negative control. The results demonstrated that compared to the vehicle treated negative control sample, the 166 compound, as a single agent, reduced the viability to 0% at a 25 uM concentration after 48 hours of treatment. At a concentration of 50 uM, viability of cells drop to 0% just at 24 hours of treatment. See FIG. 1. Cells were also treated with Cal-101 and TGR-1202 and viability was determined at 24 hr. For lower concentrations of 5 μm and 15 μM, viability dropped to ~80% for both treatments. However, as concentrations increased up to 50 μM, viability remained at ~80% for Cal-101 and modestly dropped to ~65% for TGR-1202, as shown in FIG. 1.

Example 3: CUX-03166 Reduces Viability of LY7 Cells

Figure 2:
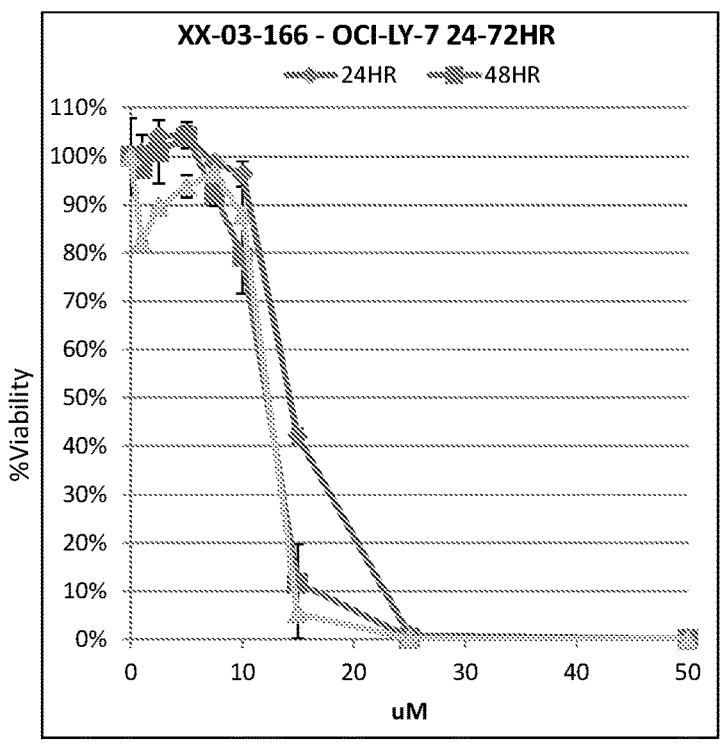
FIG. 2. CUX-03166 reduces viability of LY7 cells. The lymphoma cell line LY7 was treated with CUX-03166 for 24 hours (diamond), 48 hours (square) and 72 hours (triangle). Viability was determined similar to that for FIG. 1. At 15 uM concentrations, viability of cells dropped to 40% at 24 hours, 10% at 48 hours, and ~0% at 72 hours. At 25 uM concentrations, viability dropped to 0% at 24 hours.
Figure 3:
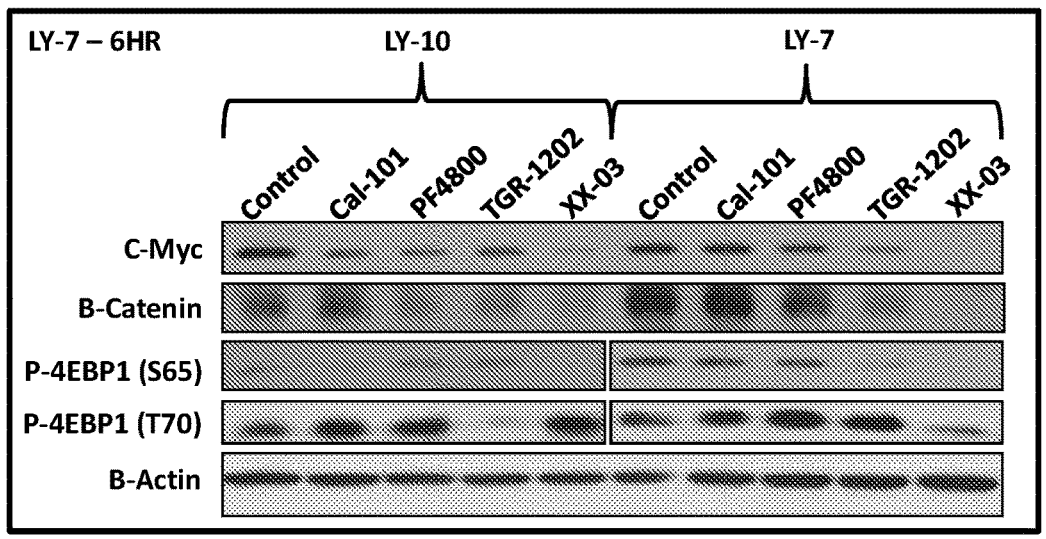
FIG. 3. CUX-03166 is more active than TGR-1202 or Cal-101 at inhibiting c-Myc in lymphoma. The lymphoma cell lines LY10 and LY7 were treated with PF4800567 (PF), Cal-101 (Cal), TGR-1202 (TG) and CUX-03166 as single agents for 6 hours, all at 25 uM concentrations. Protein extracts were processed for Western blot using antibodies against c-Myc, B-Catenin, phosphorylated 4EBP1, total 4EBP1, and beta actin. The results using the LY-10 cell line demonstrated that compared to the vehicle treated negative control sample, Cal-101, PF4800, and TGR-1202 treatment produced moderate inhibition of the c-Myc level and phosphorylation of 4EBP1. CUX-03166 showed a significantly greater reduction in c-Myc levels. Using the LY-7 cell line, Cal-101 treatment showed little reduction in c-Myc and PF4800 treatment showed modest reduction. TGR-1202 showed a significantly greater reduction in c-Myc compared to Cal-101 or PF4800. However, CUX-03166 showed c-Myc levels dropped to an undetectable level. CUX-03166 showed a near-fiftyfold increase in potency in inhibiting c-Myc compared to TGR-1202.

The lymphoma cell line LY7 was treated with CUX-03166 for 24 hr (diamond), 48 hours (square) and 72 hours (triangle). Viability was determined similar to that for Example 2. As shown in FIG. 2, at 15 uM concentrations, viability of cells dropped to 40% at 24 hours, 10% at 48 hours, and ~0% at 72 hours. At 25 uM concentrations, viability dropped to 0% at 24 hours.

Figure 4:
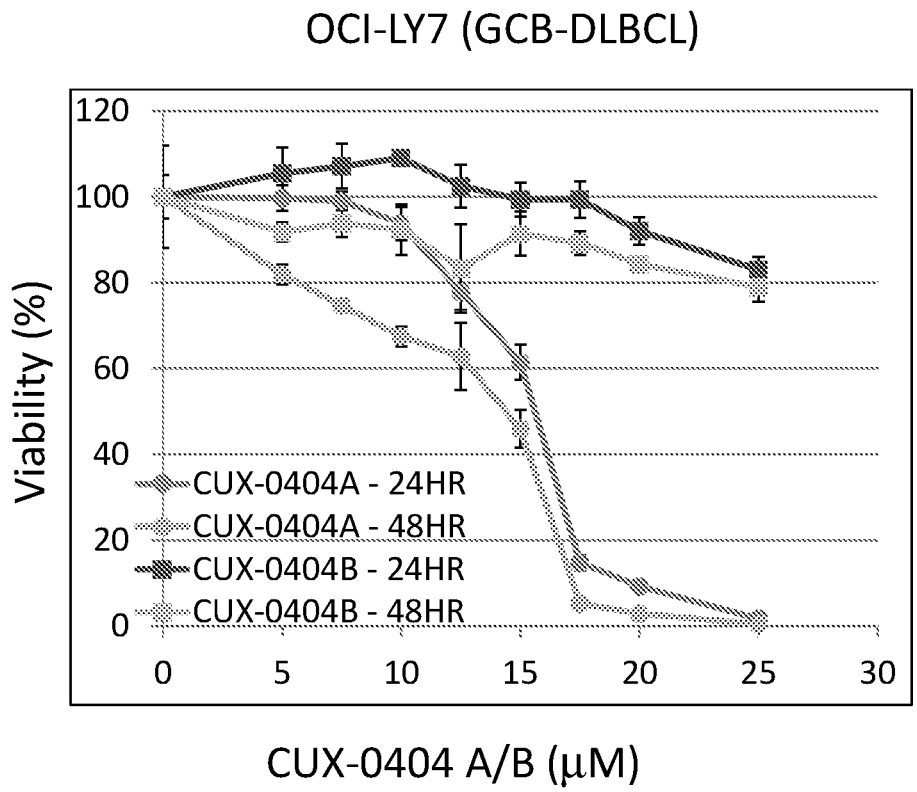
FIG. 4 CUX-0404A reduces viability of OCI-LY7 cells (germinal center diffuse large B cell lymphoma, GCB-DLBCL). The lymphoma cell line LY7 was treated with CUX-0404A for 24 hours (dark circle), 48 hours (light circle) or CUX0404B for 24 hours (dark square) or 48 hours (light square). Viability was determined similar to that for FIG. 1. At 15 uM concentrations, viability of cells dropped to 60% at 24 hours, ~42% at 48 hours, At 25 uM concentrations, viability dropped to 0% at 24 hours.

Example 4. CUX-03166 is More Active than TGR-1202 or Cal-101 at Inhibiting c-Myc in Lymphoma The lymphoma cell lines LY10 and LY7 were treated with PF4800567 (PF), Cal-101 (Cal), TGR-1202 (TG) and CUX-03166 as single agents for 6 hours all at 25 uM concentrations. Protein extracts were processed for Western blot using antibodies against c-Myc, B-Catenin, phosphorylated 4EBP1, total 4EBP1, and beta actin. As shown in FIG. 4, the results using the LY-10 cell line demonstrated that compared to the vehicle treated negative control sample, Cal-101, PF4800, and TGR-1202 treatment produced moderate inhibition of the c-Myc level and phosphorylation of 4EBP1. CUX-03166 showed a significantly greater reduction in c-Myc levels. Using the LY-7 cell line, Cal-101 treatment showed little reduction in c-Myc and PF4800 treatment showed modest reduction. TGR-1202 showed a significantly greater reduction in c-Myc compared to Cal-101 or PF4800. However, CUX-03166 showed dropped c-Myc levels down to an undetectable level. CUX-03166 showed a near-fifty-fold increase in potency in inhibiting c-Myc compared to TGR-1202.

Example 5: CUX-0404A Demonstrates Pharmacological Activity Superior to TGR-1202

Figure 5:
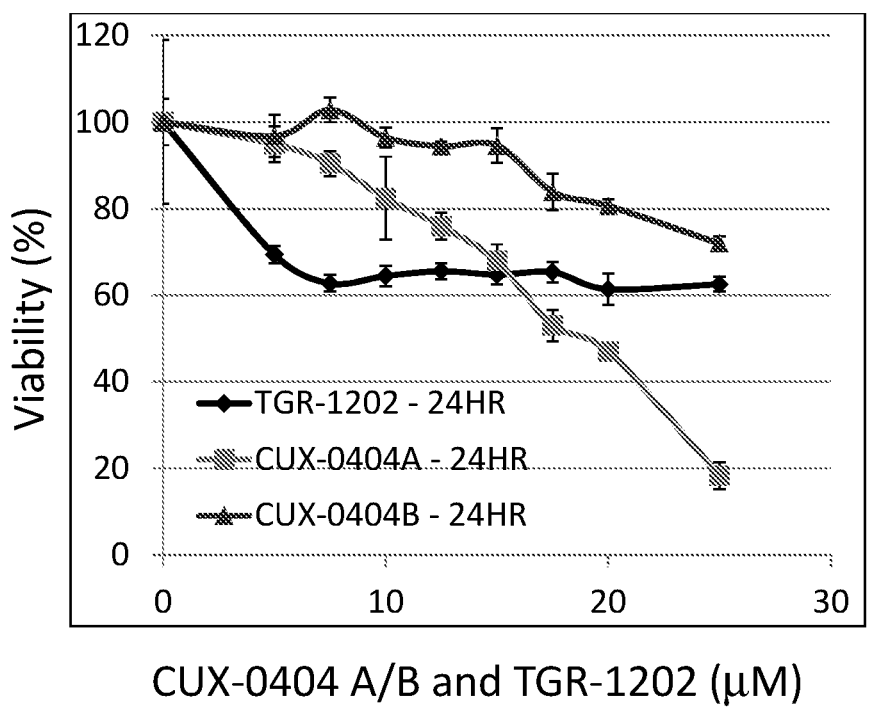
FIG. 5. CUX-0404A reduces viability of Z-138 (mantle cel lymphoma, MCL) cells more potently than TG-1202. MCL cells were treated with CUX-0404A (square), TGR-1202 (diamond) or CUX0404B (triangle) for 24 hours. Viability was determined similar to that for FIG. 1. At 25 uM concentrations, viability of cells dropped to 20% for the CUX-0404A treatment as compared to 60% for TGR-1202

CUX-0404A reduces viability of OCI-LY7 cells (germinal center diffuse large B cell lymphoma, GCB-DLBCL), see FIG. 4. The lymphoma cell line LY7 was treated with CUX-0404A for 24 hours (dark circle), 48 hours (light circle) or CUX0404B for 24 hours (dark square) or 48 hours (light square). Viability was determined similar to that for FIG. 1. At 15 uM concentrations, viability of cells dropped to 60% at 24 hours, ~42% at 48 hours, At 25 uM concentrations, viability dropped to 0% at 24 hours. FIG. 5. CUX-0404A reduces viability of Z-138 (mantle cel lymphoma, MCL) cells more potently than TG-1202. FIG. 5 shows the results of treating MCL cells were with CUX-0404A (square), TGR-1202 (diamond) or CUX0404B (triangle) for 24 hours. Viability was determined similar to that for FIG. 1. At 25 uM concentrations, viability of cells dropped to 20% for the CUX-0404A treatment as compared to 60% for TGR-1202

Figure 6:
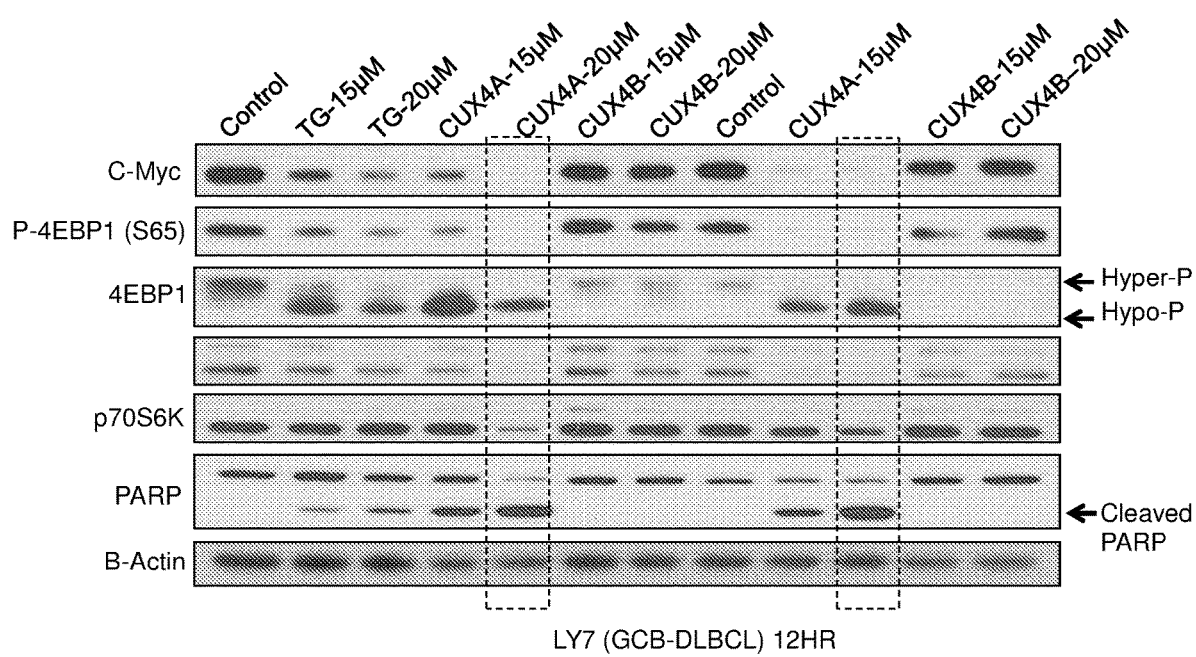
FIG. 6. CUX-0404A is more active than TGR-1202 or CUX-0404B at inhibiting c-Myc in lymphoma. The GCB-DLBCL lymphoma cell line was treated with CUX0404A (CUX4A), CUX-0404B (CUX4B), and TGR-1202 (TG) as single agents for 12 hours at 15 and 20 uM concentrations. Protein extracts were processed for Western blot using antibodies against c-Myc, B-Catenin, phosphorylated 4EBP1, total 4EBP1, P-p70S6K, P70S6K, PARP and beta actin. The results demonstrated that compared to the vehicle treated negative control sample, TGR-1202 treatment produced moderate inhibition of the c-Myc level and phosphorylation of 4EBP1. CUX-0404A showed a significantly greater reduction in c-Myc levels and c-myc was undetectable at the 20 uM concentration.

Example 6: CUX-0404A Demonstrated Potent Inhibition of Phosphorylation of 4E-BP1 and the Protein Level of c-Myc FIG. 6. CUX-0404A is more active than TGR-1202 or CUX-0404B at inhibiting c-Myc in lymphoma. FIG. 6 shows the results of treating the GCB-DLBCL lymphoma cell line with CUX0404A (CUX4A), CUX-0404B (CUX4B), and TGR-1202 (TG) as single agents for 12 hours at 15 and 20 uM concentrations. Protein extracts were processed for Western blot using antibodies against c-Myc, B-Catenin, phosphorylated 4EBP1, total 4EBP1, P-p70S6K, P70S6K, PARP and beta actin. The results demonstrated that compared to the vehicle treated negative control sample, TGR-1202 treatment produced moderate inhibition of the c-Myc level and phosphorylation of 4EBP1. CUX-0404A showed a significantly greater reduction in c-Myc levels and c-myc was undetectable at the 20 uM concentration.

Example 7: CUX-0404A has Moderate CK1epsilon Inhibition Activity

Figure 7A:
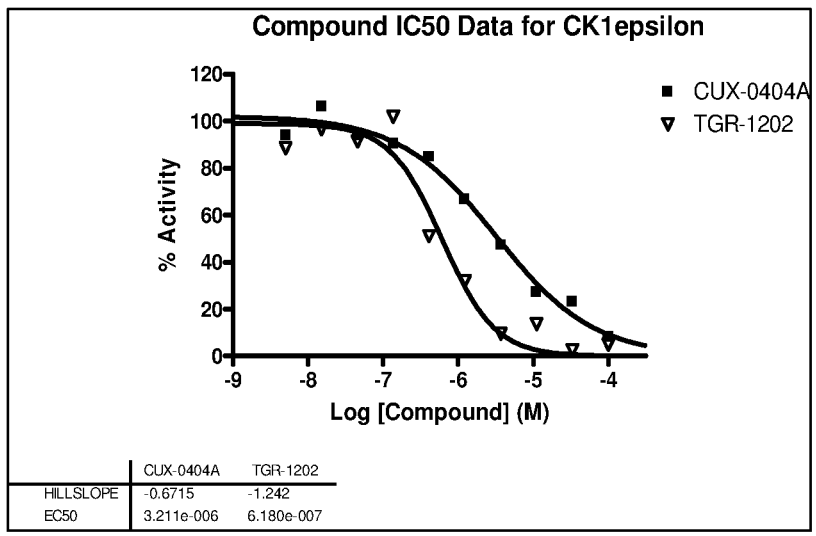
FIGS. 7A and 7B show that CUX-0404A inhibits CK1epsilon but with less potency than TGR-1202. Inhibition of CK1epsilon was tested utilizing a radioisotope filtration binding assay. Compounds were tested in 10-dose IC50 mode with 3-fold serial dilution starting at 100 μM (FIG. 7A). Control Compound, D4476, was tested in 10-dose IC50 mode with 3-fold serial dilution starting at 20 μM (FIG. 7B). Reactions were carried out at 10 μM ATP. CUX-0404A had an IC50 of 3.21 μM. TGR-1202 had an IC50 of 0.62 μM.
Figure 7B:
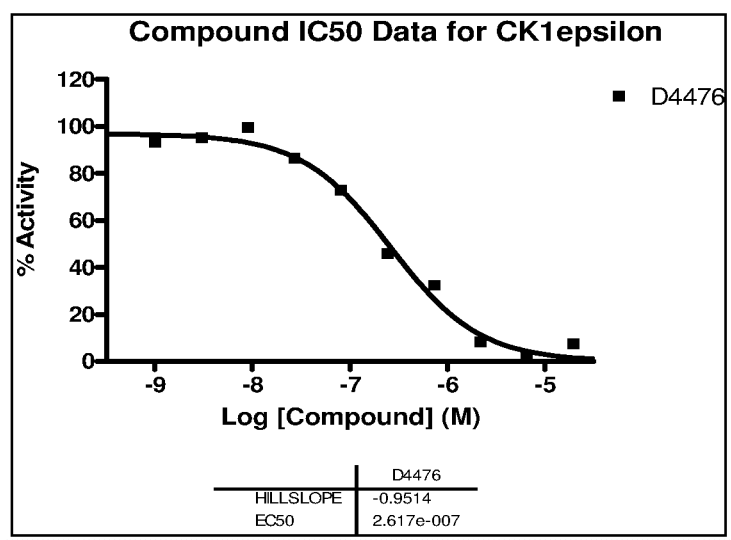

FIGS. 7A and 7B show that CUX-0404A inhibits CK1epsilon but with less potency than TGR-1202. Inhibition of CK1epsilon was tested utilizing a radioisotope filtration binding assay. Compounds were tested in 10-dose IC50 mode with 3-fold serial dilution starting at 100 μM (FIG. 7A). Control Compound, D4476, was tested in 10-dose IC50 mode with 3-fold serial dilution starting at 20 μM (FIG. 7B). Reactions were carried out at 10 μM ATP. CUX-0404A had an IC50 of 3.21 μM. TGR-1202 had an IC50 of 0.62 μM.

As will be apparent to one of ordinary skill in the art from a reading of this disclosure, further embodiments of the present invention can be presented in forms other than those specifically disclosed above. The particular embodiments described above are, therefore, to be considered as illustrative and not restrictive. Those skilled in the art will recognize, or be able to ascertain, using no more than routine experimentation, numerous equivalents to the specific embodiments described herein. Such equivalents are considered to be within the scope of this invention. Although the invention has been described and illustrated in the foregoing illustrative embodiments, it is understood that the present disclosure has been made only by way of example, and that numerous changes in the details of implementation of the invention can be made without departing from the spirit and scope of the invention, which is limited only by the claims that follow. Features of the disclosed embodiments can be combined and rearranged in various ways within the scope and spirit of the invention. The scope of the invention is as set forth in the appended claims and equivalents thereof, rather than being limited to the examples contained in the foregoing description.

TABLE 1

| | Partial list of inhibitors of the PI3K-AKT-mTOR signaling pathway | |
|---|---|---|
| Product | Description | Company |
| 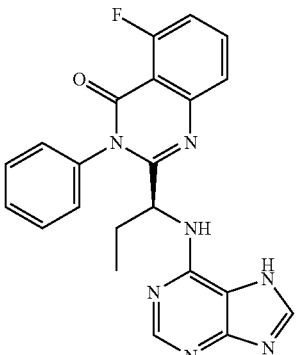<br>Idelalisib | Small molecule inhibitor of PI3Kd | Gilead Sciences Inc. (NASDAQ:GILD) |
| 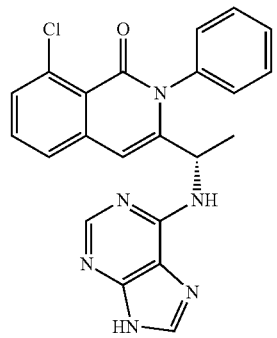<br>IPI-145, Duvelisib | Oral inhibitor of PI3Kg and PI3Kd | Takeda Pharmaceutical Co. Ltd. (Tokyo:4502)/Infinity Pharmaceuticals Inc. (NASDAQ:INFI) |
| TGR-1202 | PI3Kd inhibitor | Rhizen Pharmaceuticals S.A./TG Therapeutics Inc. (NASDAQ:TGTX) |
| 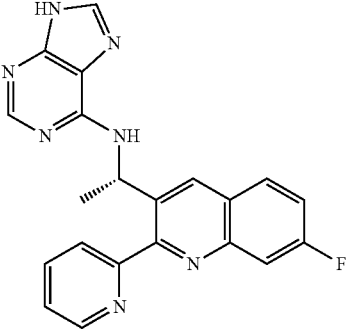<br>AMG 319 | Small molecule inhibitor of PI3Kd | Amgen Inc. (NASDAQ:AMGN) |
| INCB40093 | PI3Kd inhibitor | Incyte Corp. (NASDAQ:INCY) |

TABLE 1-continued

Partial list of inhibitors of the PI3K-AKT-mTOR signaling pathway

| Product | Description | Company |
|---|---|---|
| GS-9820 | PI3Kd inhibitor | Gilead Sciences |
| RP6530 | Dual PI3Kg and PI3Kd inhibitor | Rhizen Pharmaceuticals |
| RP6503 | Dual PI3Kg and PI3Kd inhibitor | |
| XL499 | Selective inhibitor of PI3Kd | Exelixis Inc. (NASDAQ:EXEL)/Merck & Co. Inc. (NYSE:MRK) |
| PWT143 | PI3Kd inhibitor | Pathway Therapeutics Inc./MEI Pharma Inc. (NASDAQ:MEIP) |
| X-339 | Selective inhibitor of the p110d isoform of PI3K | Xcovery Holding Co. LLC |

Other examples of PI3K inhibitors include but are not limited to: Wortmannin, demethoxyviridin, perifosine, PX-866, IPI-145 (Infinity), BAY 80-6946, BEZ235, MLN1117 (INK1117), Pictilisib, Buparlisib, SAR245408 (XL147), SAR245409 (XL765), Palomid 529, ZSTK474, PWT33597, RP6530, CUDC-907, and AEZS-136
Pan-PI3K inhibitors: BEZ235, LY294002, GDC-0941
Selective PI3K inhibitors: BYL719 (alpha); GSK263677 (beta), AS-252424 (gamma)
AKT inhibitors: MK-2206, GSK690693, GDC-0068, A-674563, CCT128930
mTOR inhibitors: AZD8055, INK128, rapamycin,
mTORC1 inhibitors: everolimus, temsirolimus, PF-04691502

TABLE 2

Partial list of adjunct chemotherapeutic agents, excluding proteasome inhibitors, that can be combined with the lead-in c-Myc silencing treatments Abiraterone Acetate
Abitrexate (Methotrexate)
Abraxane (Paclitaxel Albumin-stabilized Nanoparticle Formulation)
ABVD
ABVE
ABVE-PC
AC
AC-T
Adcetris (Brentuximab Vedotin)
ADE
Ado-Trastuzumab Emtansine
Adriamycin (Doxorubicin Hydrochloride)
Adrucil (Fluorouracil)
Afatinib Dimaleate
Afinitor (Everolimus)
Aldara (Imiquimod)
Aldesleukin
Alemtuzumab
Alimta (Pemetrexed Disodium)
Aloxi (Palonosetron Hydrochloride)
Ambochlorin (Chlorambucil)
Amboclorin (Chlorambucil)
Aminolevulinic Acid
Anastrozole
Aprepitant
Aredia (Pamidronate Disodium)
Arimidex (Anastrozole)
Aromasin (Exemes1630tane)
Arranon (Nelarabine)
Arsenic Trioxide
Arzerra (Ofatumumab)
Asparaginase Erwinia chrysanthemi
Avastin (Bevacizumab)
Axitinib
Azacitidine
BEACOPP
Becenum (Carmustine)
Beleodaq (Belinostat)
Belinostat
Bendamustine Hydrochloride
BEP
Bevacizumab
Bexarotene
Bexxar (Tositumomab and I 131 Iodine Tositumomab)
Bicalutamide
BiCNU (Carmustine)
Bleomycin
Blinatumomab
Blincyto (Blinatumomab)
Bortezomib
Bosulif (Bosutinib)
Bosutinib
Brentuximab Vedotin
Busulfan
Busulfex (Busulfan)
Cabazitaxel
Cabozantinib-S-Malate
CAF
Campath (Alemtuzumab)
Camptosar (Irinotecan Hydrochloride)
Capecitabine
CAPOX
Carboplatin
CARBOPLATIN-TAXOL
Carfilzomib
Carmubris (Carmustine)

TABLE 2-continued

Partial list of adjunct chemotherapeutic agents, excluding proteasome inhibitors, that can be combined with the lead-in c-Myc silencing treatments Carmustine
Carmustine Implant
Casodex (Bicalutamide)
CeeNU (Lomustine)
Ceritinib
Cerubidine (Daunorubicin Hydrochloride)
Cervarix (Recombinant HPV Bivalent Vaccine)
Cetuximab
Chlorambucil
CHLORAMBUCIL-PREDNISONE
CHOP
Cisplatin
Clafen (Cyclophosphamide)
Clofarabine
Clofarex (Clofarabine)
Clolar (Clofarabine)
CMF
Cometriq (Cabozantinib-S-Malate)
COPP
COPP-ABV
Cosmegen (Dactinomycin)
Crizotinib
CVP
Cyclophosphamide
Cyfos (Ifosfamide)
Cyramza (Ramucirumab)
Cytarabine
Cytarabine, Liposomal
Cytosar-U (Cytarabine)
Cytoxan (Cyclophosphamide)
Dabrafenib
Dacarbazine
Dacogen (Decitabine)
Dactinomycin
Dasatinib
Daunorubicin Hydrochloride
Decitabine
Degarelix
Denileukin Diftitox
Denosumab
Dinutuximab
DepoCyt (Liposomal Cytarabine)
DepoFoam (Liposomal Cytarabine)
Dexrazoxane Hydrochloride
Docetaxel
Doxil (Doxorubicin Hydrochloride Liposome)
Doxorubicin Hydrochloride
Doxorubicin Hydrochloride Liposome
Dox-SL (Doxorubicin Hydrochloride Liposome)
DTIC-Dome (Dacarbazine)
Efudex (Fluorouracil)
Elitek (Rasburicase)
Ellence (Epirubicin Hydrochloride)
Eloxatin (Oxaliplatin)
Eltrombopag Olamine
Emend (Aprepitant)
Enzalutamide
Epirubicin Hydrochloride
EPOCH
Erbitux (Cetuximab)
Eribulin Mesylate
Erivedge (Vismodegib)
Erlotinib Hydrochloride
Erwinaze (Asparaginase Erwinia chrysanthemi)
Etopophos (Etoposide Phosphate)
Etoposide
Etoposide Phosphate
Evacet (Doxorubicin Hydrochloride Liposome)
Everolimus
Evista (Raloxifene Hydrochloride)
Exemestane
Fareston (Toremifene)
Farydak (Panobinostat)
Faslodex (Fulvestrant)
FEC
Femara (Letrozole)
Filgrastim
Fludara (Fludarabine Phosphate)
Fludarabine Phosphate
Fluoroplex (Fluorouracil)
Fluorouracil
Folex (Methotrexate)
Folex PFS (Methotrexate)
FOLFIRI
FOLFIRI-BEVACIZUMAB
FOLFIRI-CETUXIMAB
FOLFIRINOX
FOLFOX
Folotyn (Pralatrexate)
FU-LV
Fulvestrant
Gardasil (Recombinant HPV Quadrivalent Vaccine)
Gardasil 9 (Recombinant HPV Nonavalent Vaccine)
Gazyva (Obinutuzumab)
Gefitinib
Gemcitabine Hydrochloride
GEMCITABINE-CISPLATIN
GEMCITABINE-OXALIPLATIN
Gemtuzumab Ozogamicin
Gemzar (Gemcitabine Hydrochloride)
Gilotrif (Afatinib Dimaleate)
Gleevec (Imatinib Mesylate)
Gliadel (Carmustine Implant)
Gliadel wafer (Carmustine Implant)
Glucarpidase
Goserelin Acetate
Halaven (Eribulin Mesylate)
Herceptin (Trastuzumab)
HPV Bivalent Vaccine, Recombinant
HPV Nonavalent Vaccine, Recombinant
HPV Quadrivalent Vaccine, Recombinant
Hycamtin (Topotecan Hydrochloride)
Hyper-CVAD
Ibrance (Palbociclib)
Ibritumomab Tiuxetan
Ibrutinib
ICE
Iclusig (Ponatinib Hydrochloride)
Idamycin (Idarubicin Hydrochloride)
Idarubicin Hydrochloride
Idelalisib
Ifex (Ifosfamide)
Ifosfamide
Ifosfamidum (Ifosfamide)
Imatinib Mesylate
Imbruvica (Ibrutinib)
Imiquimod
Inlyta (Axitinib)
Intron A (Recombinant Interferon Alfa-2b)
Iodine 131 Tositumomab and Tositumomab
Ipilimumab
Iressa (Gefitinib)
Irinotecan Hydrochloride
Istodax (Romidepsin)
Ixabepilone
Ixempra (Ixabepilone)
Jakafi (Ruxolitinib Phosphate)
Jevtana (Cabazitaxel)
Kadcyla (Ado-Trastuzumab Emtansine)
Keoxifene (Raloxifene Hydrochloride)
Kepivance (Palifermin)
Keytruda (Pembrolizumab)
Kyprolis (Carfilzomib)
Lanreotide Acetate
Lapatinib Ditosylate
Lenalidomide
Lenvatinib Mesylate
Lenvima (Lenvatinib Mesylate)
Letrozole
Leucovorin Calcium
Leukeran (Chlorambucil)
Leuprolide Acetate TABLE 2-continued Partial list of adjunct chemotherapeutic agents, excluding proteasome inhibitors, that can be combined with the lead-in c-Myc silencing treatments Levulan (Aminolevulinic Acid)
Linfolizin (Chlorambucil)
LipoDox (Doxorubicin Hydrochloride Liposome)
Liposomal Cytarabine
Lomustine
Lupron (Leuprolide Acetate)
Lupron Depot (Leuprolide Acetate)
Lupron Depot-Ped (Leuprolide Acetate)
Lupron Depot-3 Month (Leuprolide Acetate)
Lupron Depot-4 Month (Leuprolide Acetate)
Lynparza (Olaparib)
Marqibo (Vincristine Sulfate Liposome)
Matulane (Procarbazine Hydrochloride)
Mechlorethamine Hydrochloride
Megace (Megestrol Acetate)
Megestrol Acetate
Mekinist (Trametinib)
Mercaptopurine
Mesna
Mesnex (Mesna)
Methazolastone (Temozolomide)
Methotrexate
Methotrexate LPF (Methotrexate)
Mexate (Methotrexate)
Mexate-AQ (Methotrexate)
Mitomycin C
Mitoxantrone Hydrochloride
Mitozytrex (Mitomycin C)
MOPP
Mozobil (Plerixafor)
Mustargen (Mechlorethamine Hydrochloride)
Mutamycin (Mitomycin C)
Myleran (Busulfan)
Mylosar (Azacitidine)
Mylotarg (Gemtuzumab Ozogamicin)
Nanoparticle Paclitaxel (Paclitaxel Albumin-stabilized Nanoparticle Formulation)
Navelbine (Vinorelbine Tartrate)
Nelarabine
Neosar (Cyclophosphamide)
Neupogen (Filgrastim)
Nexavar (Sorafenib Tosylate)
Nilotinib
Nivolumab
Nolvadex (Tamoxifen Citrate)
Nplate (Romiplostim)
Obinutuzumab
OEPA
Ofatumumab
OFF
Olaparib
Omacetaxine Mepesuccinate
Oncaspar (Pegaspargase)
Ontak (Denileukin Diftitox)
Opdivo (Nivolumab)
OPPA
Oxaliplatin
Paclitaxel
Paclitaxel Albumin-stabilized Nanoparticle Formulation
PAD
Palbociclib
Palifermin
Palonosetron Hydrochloride
Pamidronate Disodium
Panitumumab
Panobinostat
Paraplat (Carboplatin)
Paraplatin (Carboplatin)
Pazopanib Hydrochloride
Pegaspargase
Peginterferon Alfa-2b
PEG-Intron (Peginterferon Alfa-2b)
Pembrolizumab
Pemetrexed Disodium
Perjeta (Pertuzumab)
Pertuzumab
Platinol (Cisplatin)
Platinol-AQ (Cisplatin)
Plerixafor
Pomalidomide
Pomalyst (Pomalidomide)
Ponatinib Hydrochloride
Pralatrexate
Prednisone
Procarbazine Hydrochloride
Proleukin (Aldesleukin)
Prolia (Denosumab)
Promacta (Eltrombopag Olamine)
Provenge (Sipuleucel-T)
Purinethol (Mercaptopurine)
Purixan (Mercaptopurine)
Radium 223 Dichloride
Raloxifene Hydrochloride
Ramucirumab
Rasburicase
R-CHOP
R-CVP
Recombinant Human Papillomavirus (HPV) Bivalent Vaccine
Recombinant Human Papillomavirus (HPV) Nonavalent Vaccine
Recombinant Human Papillomavirus (HPV) Quadrivalent Vaccine
Recombinant Interferon Alfa-2b
Regorafenib
R-EPOCH
Revlimid (Lenalidomide)
Rheumatrex (Methotrexate)
Rituxan (Rituximab)
Rituximab
Romidepsin
Romiplostim
Rubidomycin (Daunorubicin Hydrochloride)
Ruxolitinib Phosphate
Sclerosol Intrapleural Aerosol (Talc)
Siltuximab
Sipuleucel-T
Somatuline Depot (Lanreotide Acetate)
Sorafenib Tosylate
Sprycel (Dasatinib)
STANFORD V
Sterile Talc Powder (Talc)
Steritalc (Talc)
Stivarga (Regorafenib)
Sunitinib Malate
Sutent (Sunitinib Malate)
Sylatron (Peginterferon Alfa-2b)
Sylvant (Siltuximab)
Synovir (Thalidomide)
TAC
Tafinlar (Dabrafenib)
Talc
Tamoxifen Citrate
Tarabine PFS (Cytarabine)
Tarceva (Erlotinib Hydrochloride)
Targretin (Bexarotene)
Tasigna (Nilotinib)
Taxol (Paclitaxel)
Taxotere (Docetaxel)
Temodar (Temozolomide)
Temozolomide
Temsirolimus
Thalidomide
Thalomid (Thalidomide)
Thiotepa
Toposar (Etoposide)
Topotecan Hydrochloride
Toremifene
Torisel (Temsirolimus)
Tositumomab and I 131 Iodine Tositumomab
Totect (Dexrazoxane Hydrochloride)
TPF
Trametinib
Trastuzumab
Treanda (Bendamustine Hydrochloride)

TABLE 2-continued

Partial list of adjunct chemotherapeutic agents, excluding proteasome inhibitors, that can be combined with the lead-in c-Myc silencing treatments Trisenox (Arsenic Trioxide)
Tykerb (Lapatinib Ditosylate)
Unituxin (Dinutuximab)
Vandetanib
VAMP
Vectibix (Panitumumab)
VeIP
Velban (Vinblastine Sulfate)
Velcade (Bortezomib)
Velsar (Vinblastine Sulfate)
Vemurafenib
VePesid (Etoposide)
Viadur (Leuprolide Acetate)
Vidaza (Azacitidine)
Vinblastine Sulfate
Vincasar PFS (Vincristine Sulfate)
Vincristine Sulfate
Vincristine Sulfate Liposome
Vinorelbine Tartrate
VIP
Vismodegib
Voraxaze (Glucarpidase)
Vorinostat
Votrient (Pazopanib Hydrochloride)
Wellcovorin (Leucovorin Calcium)
Xalkori (Crizotinib)
Xeloda (Capecitabine)
XELIRI
XELOX
Xgeva (Denosumab)
Xofigo (Radium 223 Dichloride)
Xtandi (Enzalutamide)
Yervoy (Ipilimumab)
Zaltrap (Ziv-Aflibercept)
Zelboraf (Vemurafenib)
Zevalin (Ibritumomab Tiuxetan)
Zinecard (Dexrazoxane Hydrochloride)
Ziv-Aflibercept
Zoladex (Goserelin Acetate)
Zoledronic Acid
Zolinza (Vorinostat)
Zometa (Zoledronic Acid)
Zydelig (Idelalisib)
Zykadia (Ceritinib)
Zytiga (Abiraterone Acetate)

TABLE 3

Casein Kinase inhibitors

Product Name/Activity

CKI 7 dihydrochloride - CK1 inhibitor

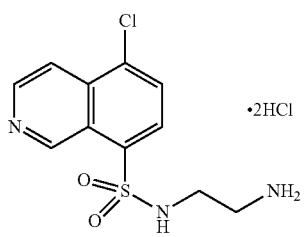 [SMILES: NCCNS(=O)(=O)c1ccc(Cl)c2ccncc12]

(R)-CR8 - Dual cdk/CK1 inhibitor

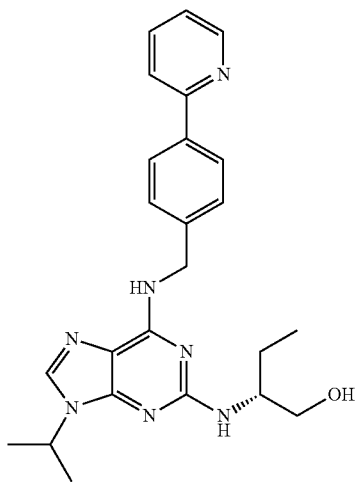 [SMILES: CC[C@H](CO)Nc1nc(NCc2ccc(-c3ccccn3)cc2)c2ncn(C(C)C)c2n1]

D 4476 - Selective CK1 inhibitor. Also inhibits TGF-βRI

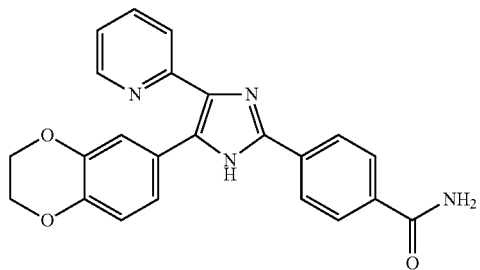 [SMILES: NC(=O)c1ccc(-c2nc(-c3ccccn3)c(-c3ccc4c(c3)OCCO4)[nH]2)cc1]

(R)-DRF053 dihydrochloride - Dual CK1/cdk inhibitor

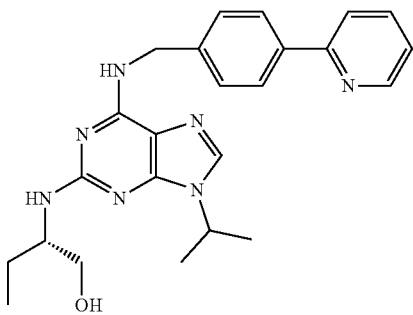 [SMILES: CC[C@@H](CO)Nc1nc(NCc2ccc(-c3ccccn3)cc2)c2ncn(C(C)C)c2n1]

TABLE 3-continued

Casein Kinase inhibitors

Product Name/Activity

PF 4800567 hydrochloride - Selective casein kinase 1ε inhibitor

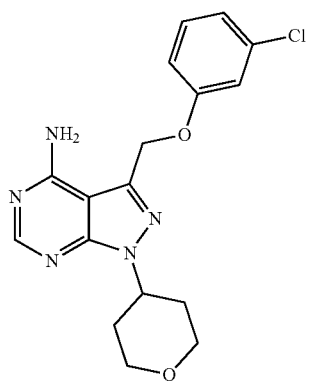 [SMILES: Nc1ncnc2c1c(COc1cccc(Cl)c1)nn2C1CCOCC1]

PF 670462 - Potent and selective CK1ε and CK1δ inhibitor

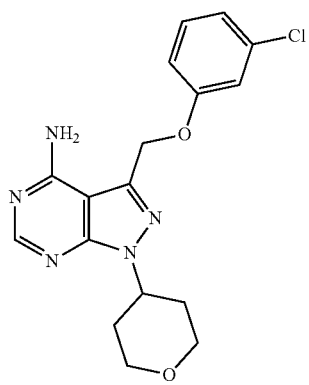 [SMILES: Nc1ncnc2c1c(COc1cccc(Cl)c1)nn2C1CCOCC1]

TA 01 - CK1ε and CK1δ inhibitor; also inhibits p38α

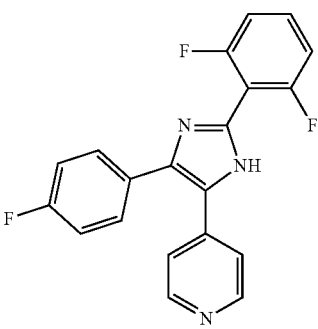 [SMILES: Fc1ccc(-c2nc(-c3c(F)cccc3F)[nH]c2-c2ccncc2)cc1]

TABLE 3-continued

Casein Kinase inhibitors

Product Name/Activity

TA 02 - CK1ε and CK1δ inhibitor; also inhibits p38α

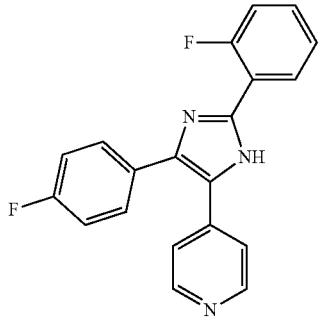 [SMILES: Fc1ccc(-c2nc(-c3ccccc3F)[nH]c2-c2ccncc2)cc1]

TAK 715 - Inhibitor of Wnt/β-catenin signaling; cross-reacts with CK1δ/ε

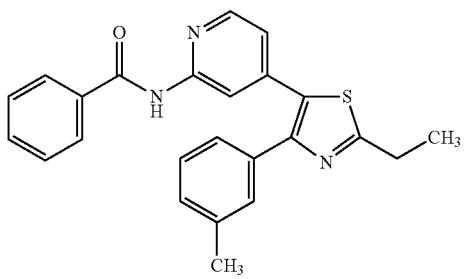 [SMILES: CCc1nc(-c2cccc(C)c2)c(-c2ccnc(NC(=O)c3ccccc3)c2)s1]

LH 846-CK1 delta

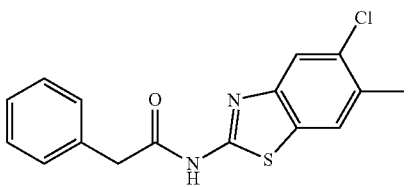

Lenalidomide-CK1 alpha

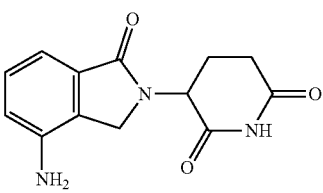 [SMILES: Nc1cccc2c1CN(C1CCC(=O)NC1=O)C2=O]

REFERENCES

All publications mentioned herein are incorporated by reference in their entirety.

1. Dang, C. V., MYC, metabolism, cell growth, and tumorigenesis. Cold Spring Harb Perspect Med, 2013. 3(8).
2. Chisholm, K. M., et al., Expression profiles of MYC protein and MYC gene rearrangement in lymphomas. Am J Surg Pathol, 2015. 39(3): p. 294-303.
3. Sehn, L. H., A decade of R-CHOP. Blood. 116(12): p. 2000-1.

4. Rosenwald, A., et al., The use of molecular profiling to predict survival after chemotherapy for diffuse large-B-cell lymphoma. N Engl J Med, 2002. 346(25): p. 1937-47.
5. Savage, K. J., et al., MYC gene rearrangements are associated with a poor prognosis in diffuse large B-cell lymphoma patients treated with R-CHOP chemotherapy. Blood, 2009. 114(17): p. 3533-7.
6. Barrans, S., et al., Rearrangement of MYC is associated with poor prognosis in patients with diffuse large B-cell lymphoma treated in the era of rituximab. J Clin Oncol, 2010. 28(20): p. 3360-5.
7. Johnson, N. A., et al., Concurrent expression of MYC and BCL2 in diffuse large B-cell lymphoma treated with rituximab plus cyclophosphamide, doxorubicin, vincristine, and prednisone. J Clin Oncol, 2012. 30(28): p. 3452-9.
8. Green, T. M., et al., Immunohistochemical double-hit score is a strong predictor of outcome in patients with diffuse large B-cell lymphoma treated with rituximab plus cyclophosphamide, doxorubicin, vincristine, and prednisone. J Clin Oncol, 2012. 30(28): p. 3460-7.
9. Hu, S., et al., MYC/BCL2 protein coexpression contributes to the inferior survival of activated B-cell subtype of diffuse large B-cell lymphoma and demonstrates high-risk gene expression signatures: a report from The International DLBCL Rituximab-CHOP Consortium Program. Blood, 2013. 121(20): p. 4021-31; quiz 4250.
10. Petrich, A. M., C. Nabhan, and S. M. Smith, MYC-associated and double-hit lymphomas: a review of pathobiology, prognosis, and therapeutic approaches. Cancer, 2014. 120(24): p. 3884-95.
11. Petrich, A. M., et al., Impact of induction regimen and stem cell transplantation on outcomes in double-hit lymphoma: a multicenter retrospective analysis. Blood, 2014. 124(15): p. 2354-61.
12. Lin, P. and L. J. Medeiros, High-grade B-cell lymphoma/leukemia associated with t(14;18) and 8q24/MYC rearrangement: a neoplasm of germinal center immunophenotype with poor prognosis. Haematologica, 2007. 92(10): p. 1297-301.
13. Andresen, C., et al., Transient structure and dynamics in the disordered c-Myc transactivation domain affect Bin1 binding. Nucleic Acids Res, 2012. 40(13): p. 6353-66.
14. Lin, C. J., et al., c-Myc and eIF4F are components of a feedforward loop that links transcription and translation. Cancer Res, 2008. 68(13): p. 5326-34.
15. Wolfe, A. L., et al., RNA G-quadruplexes cause eIF4A-dependent oncogene translation in cancer. Nature, 2014. 513(7516): p. 65-70.
16. Fingar, D. C., et al., Mammalian cell size is controlled by mTOR and its downstream targets S6K1 and 4EBP1/eIF4E. Genes Dev, 2002. 16(12): p. 1472-87.
17. Hutter, G., et al., Proteasome inhibition leads to dephosphorylation and downregulation of protein expression of members of the Akt/mTOR pathway in MCL. Leukemia, 2012. 26(11): p. 2442-4.
18. Quy, P. N., et al., Proteasome-dependent activation of mammalian target of rapamycin complex 1 (mTORC1) is essential for autophagy suppression and muscle remodeling following denervation. J Biol Chem, 2013. 288(2): p. 1125-34.
19. Tang, B., et al., Proteasome Inhibitors Activate Autophagy Involving Inhibition of PI3K-Akt-mTOR Pathway as an Anti-Oxidation Defense in Human RPE Cells. PLoS One, 2014. 9(7): p. e103364.
20. Zhang, Y., et al., Coordinated regulation of protein synthesis and degradation by mTORC1. Nature, 2014. 513(7518): p. 440-3.
21. Pourdehnad, M., et al., Myc and mTOR converge on a common node in protein synthesis control that confers synthetic lethality in Myc-driven cancers. Proc Natl Acad Sci USA, 2013. 110(29): p. 11988-93.
22. Deng, C., et al., The novel IKK2 inhibitor LY2409881 potently synergizes with histone deacetylase inhibitors in preclinical models of lymphoma through the downregulation of NF-kappaB. Clin Cancer Res, 2015. 21(1): p. 134-45.
23. Herman, S. E., et al., Phosphatidylinositol 3-kinase-delta inhibitor CAL-101 shows promising preclinical activity in chronic lymphocytic leukemia by antagonizing intrinsic and extrinsic cellular survival signals. Blood, 2010. 116(12): p. 2078-88.
24. Lannutti, B. J., et al., CAL-101, a p110delta selective phosphatidylinositol-3-kinase inhibitor for the treatment of B-cell malignancies, inhibits PI3K signaling and cellular viability. Blood, 2011. 117(2): p. 591-4.
25. Gopal, A. K., et al., PI3Kdelta inhibition by idelalisib in patients with relapsed indolent lymphoma. The New England journal of medicine, 2014. 370(11): p. 1008-18.
26. Furman, R. R., et al., Idelalisib and Rituximab in Relapsed Chronic Lymphocytic Leukemia. N Engl J Med, 2014.
27. Burris III, H., et al., TGR-1202, a Novel Once Daily PI3Kδ Inhibitor, Demonstrates Clinical Activity with a Favorable Safety Profile, Lacking Hepatotoxicity, in Patients with CLL and B-Cell Lymphoma. European Hematology Association Annual Meeting, 2015. Abstract and Presentation.
28. Borisy, A. A., et al., Systematic discovery of multicomponent therapeutics. Proc Natl Acad Sci USA, 2003. 100(13): p. 7977-82.
29. Oliver, F. J., et al., Importance of poly(ADP-ribose) polymerase and its cleavage in apoptosis. Lesson from an uncleavable mutant. J Biol Chem, 1998. 273(50): p. 33533-9.
30. Yang, Z., N. He, and Q. Zhou, Brd4 recruits P-TEFb to chromosomes at late mitosis to promote G1 gene expression and cell cycle progression. Mol Cell Biol, 2008. 28(3): p. 967-76.
31. Dey, A., et al., Brd4 marks select genes on mitotic chromatin and directs postmitotic transcription. Mol Biol Cell, 2009. 20(23): p. 4899-909.
32. Filippakopoulos, P., et al., Selective inhibition of BET bromodomains. Nature, 2010. 468(7327): p. 1067-73.
33. Mertz, J. A., et al., Targeting MYC dependence in cancer by inhibiting BET bromodomains. Proc Natl Acad Sci USA, 2011. 108(40): p. 16669-74.
34. Zuber, J., et al., RNAi screen identifies Brd4 as a therapeutic target in acute myeloid leukaemia. Nature, 2011. 478(7370): p. 524-8.
35. Delmore, J. E., et al., BET bromodomain inhibition as a therapeutic strategy to target c-Myc. Cell, 2011. 146(6): p. 904-17.
36. Ott, C. J., et al., BET bromodomain inhibition targets both c-Myc and IL7R in high-risk acute lymphoblastic leukemia. Blood, 2012. 120(14): p. 2843-52.
37. Bordeleau, M. E., et al., Therapeutic suppression of translation initiation modulates chemosensitivity in a mouse lymphoma model. J Clin Invest, 2008. 118(7): p. 2651-60.

38. Cencic, R., et al., Reversing chemoresistance by small molecule inhibition of the translation initiation complex eIF4F. Proc Natl Acad Sci USA, 2011. 108(3): p. 1046-51.
39. Moerke, N.J., et al., Small-molecule inhibition of the interaction between the translation initiation factors eIF4E and eIF4G. Cell, 2007. 128(2): p. 257-67.
40. Boussemart, L., et al., eIF4F is a nexus of resistance to anti-BRAF and anti-MEK cancer therapies. Nature, 2014. 513(7516): p. 105-9.
41. Low, W. K., et al., Second-generation derivatives of the eukaryotic translation initiation inhibitor pateamine A targeting eIF4A as potential anticancer agents. Bioorg Med Chem, 2014. 22(1): p. 116-25.
42. Cencic, R., et al., Antitumor activity and mechanism of action of the cyclopenta[b]benzofuran, silvestrol. PLoS One, 2009. 4(4): p. e5223.
43. Duan, S., et al., mTOR generates an auto-amplification loop by triggering the betaTrCP- and CK1alpha-dependent degradation of DEPTOR. Mol Cell, 2011. 44(2): p. 317-24.
44. Zhao, Y., X. Xiong, and Y. Sun, DEPTOR, an mTOR inhibitor, is a physiological substrate of SCF(betaTrCP) E3 ubiquitin ligase and regulates survival and autophagy. Mol Cell, 2011. 44(2): p. 304-16.
45. Gao, D., et al., mTOR drives its own activation via SCF(betaTrCP)-dependent degradation of the mTOR inhibitor DEPTOR. Mol Cell, 2011. 44(2): p. 290-303.
46. Hutter, G., et al., The proteasome inhibitor bortezomib targets cell cycle and apoptosis and acts synergistically in a sequence-dependent way with chemotherapeutic agents in mantle cell lymphoma. Ann Hematol, 2012. 91(6): p. 847-56.
47. Burris, H. A., et al., TGR-1202, a Novel Once Daily PI3Kδ Inhibitor, Demonstrates Clinical Activity with a Favorable Safety Profile, Lacking Hepatotoxicity, in Patients with Chronic Lymphocytic Leukemia and B-Cell Lymphoma. Vol. 124. 2014. 1984-1984.
48. O'Connor, O. A., et al., A phase 1 dose escalation study of the safety and pharmacokinetics of the novel proteasome inhibitor carfilzomib (PR-171) in patients with hematologic malignancies. Clinical cancer research: an official journal of the American Association for Cancer Research, 2009. 15(22): p. 7085-91.
49. Cegielska, A., Gietzen, K. F., Rivers, A., and Virshup, D. M. (1998). Autoinhibition of casein kinase I epsilon (CKI epsilon) is relieved by protein phosphatases and limited proteolysis. J Biol Chem 273, 1357-1364.
50. Cheong, J. K., Nguyen, T. H., Wang, H., Tan, P., Voorhoeve, P. M., Lee, S. H., and Virshup, D. M. (2011). IC261 induces cell cycle arrest and apoptosis of human cancer cells via CK1delta/varepsilon and Wnt/beta-catenin independent inhibition of mitotic spindle formation. Oncogene 30, 2558-2569.
51. Rivers, A., Gietzen, K. F., Vielhaber, E., and Virshup, D. M. (1998). Regulation of casein kinase I epsilon and casein kinase I delta by an in vivo futile phosphorylation cycle. J Biol Chem 273, 15980-15984.
52. Deng, C., McIntosh, C., Rodriguez, R., Sportelli, P., Miskin, H. P., Vakkalanka, S., Viswanadha, S., Lipstein, M., and O'Connor, O. A. (2013). The PI3K Delta Inhibitor TGR-1202 and Proteasome Inhibitor Carfilzomib Are Highly Synergistic In Killing Human B- and T-Cell Lymphoma Cells. Blood 122, 4421.
53. Long, A. M., Zhao, H., and Huang, X. (2012). Structural basis for the potent and selective inhibition of casein kinase 1 epsilon. J Med Chem 55, 10307-10311.

What is claimed is:

1. A compound according to Formula I or Formula II:

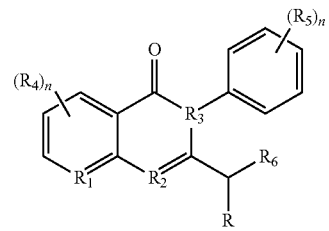

Formula I

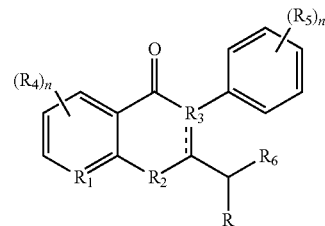

Formula II or a pharmaceutically acceptable salt thereof, wherein R is H or any one of groups A-G:

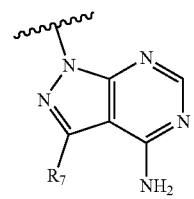

A

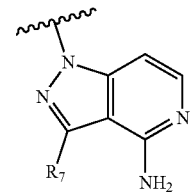

B

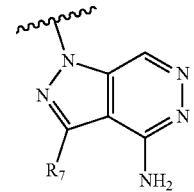

C

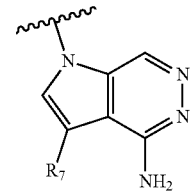

D

-continued

E

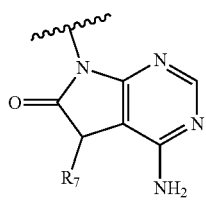

F

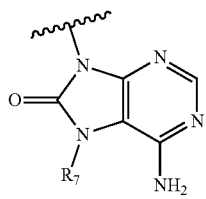

G

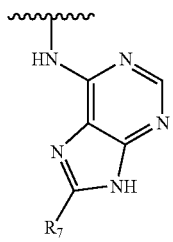

and wherein

=== represents a single or double bond;

R$_1$ is N;

R$_2$
- in the compound of Formula I is CH, substituted C or N;
- in the compound of Formula II is O, CH$_2$, substituted C, NH or substituted N;

R$_3$
- in the compound of Formula I is CH, substituted C or N;
- in the compound of Formula II is
  - CH, substituted C or N when === represents a single bond; or
  - C when === represents a double bond;

each R$_4$ is independently substituted alkyl, unsubstituted alkyl, substituted alkenyl, unsubstituted alkenyl, substituted alkynyl, unsubstituted alkynyl, or halogen;

each R$_5$ is independently substituted alkyl, unsubstituted alkyl, substituted alkenyl, unsubstituted alkenyl, substituted alkynyl, unsubstituted alkynyl, or halogen;

R$_6$ is substituted C$_{2-10}$alkyl or unsubstituted C$_{2-10}$alkyl;

R$_7$ is H or a group selected from any one of groups J, K and H

J

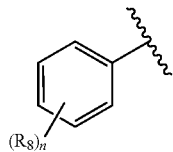

-continued

K

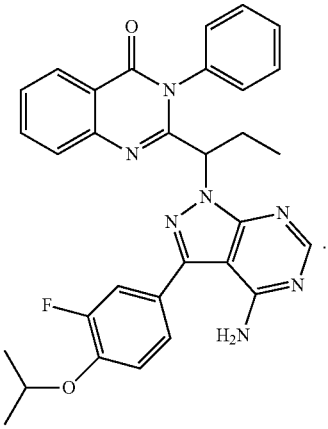 [SMILES: CCC(c1nc2ccccc2c(=O)n1-c1ccccc1)n1nc(-c2ccc(OC(C)C)c(F)c2)c2c(N)ncnc21]

H and each R$_8$ is independently substituted alkyl, unsubstituted alkyl, substituted O-alkyl, unsubstituted O-alkyl or halogen;

n for R$_4$ and when R$_1$ is not N, is 0, 1, 2, 3 or 4;

n for R$_4$ and when R$_1$ is N, is 0, 1, 2 or 3;

n for R$_5$ is 0, 1, 2, 3, 4 or 5; and n for R$_8$ is 0, 1, 2, 3, 4 or 5;

with the provisos that

R$_7$ is not H when R is group G;

the following compound is excluded:

2. The compound of claim 1 wherein the following compounds are further excluded:
   compounds of formula I wherein at the same time R is group A, R$_3$ is N and R$_7$ is J;
   compounds of formula II wherein at the same time R is group A, R$_2$ is O, R$_3$ is C, === represents a double bond, and R$_7$ is J.

3. The compound of claim 1 wherein R$_6$ is substituted C$_{3-10}$alkyl or unsubstituted C$_{3-10}$alkyl.

4. The compound of claim 3 wherein R$_6$ is substituted or unsubstituted propyl, substituted or unsubstituted butyl, or substituted or unsubstituted ethyl.

5. The compound of claim 1, wherein n for R$_4$ is 1 or 2 and at least one R$_4$ is halogen.

6. The compound of claim 5 wherein halogen is F.

7. The compound of claim 6 wherein n for R$_4$ is 1, and R$_4$ is located at position 5 of the quinazolin-4-one ring to which it is attached.

8. The compound of claim 1, wherein n for $R_5$ is 0.

9. The compound of claim 1, wherein R is group A.

10. The compound of claim 1, wherein $R_7$ is J, or is not J.

11. The compound of any of claim 1, wherein n for $R_8$ is 2, one $R_8$ is isopropyl or O-isopropyl, and the other $R_8$ is halogen.

12. The compound of claim 1, wherein $R_7$ is one of the following:

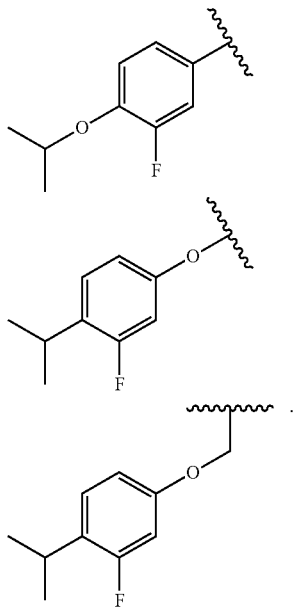

13. The compound of claim 1 which is a compound according to the following formula:

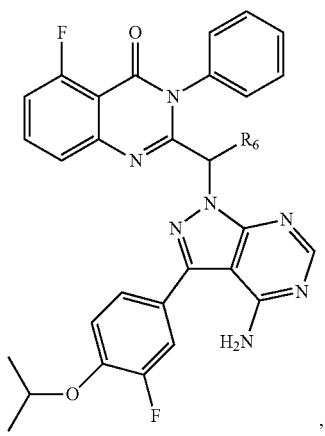

wherein $R_6$ is substituted $C_{2-10}$alkyl or unsubstituted $C_{2-10}$alkyl.

14. The compound of claim 13 wherein $R_6$ is substituted or unsubstituted propyl, substituted or unsubstituted butyl, or substituted or unsubstituted ethyl.

15. The compound of claim 14 wherein $R_6$ is unsubstituted ethyl.

16. A compound according to Formula I or Formula II:

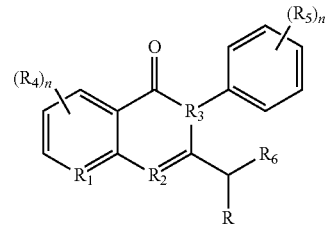

Formula I

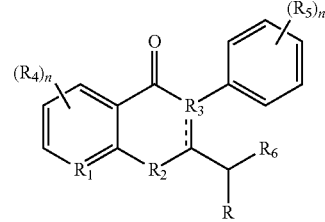

Formula II or a pharmaceutically acceptable salt thereof, wherein R is H or any one of groups A-G:

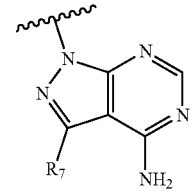

A

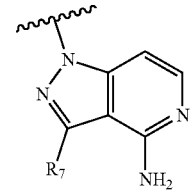

B

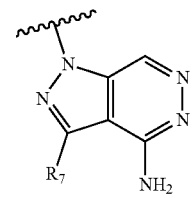

C

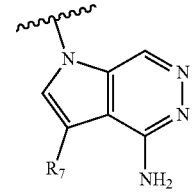

D

-continued

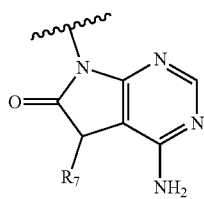
E

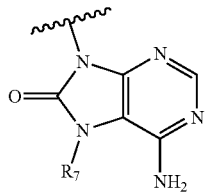
F

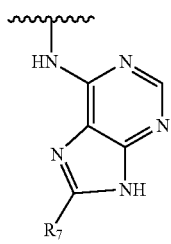
G and wherein
═══ represents a single or double bond;
R$_1$, R$_2$, and R$_3$ are N;
R$_4$ is each independently substituted alkyl, unsubstituted alkyl, substituted alkenyl, unsubstituted alkenyl, substituted alkynyl, unsubstituted alkynyl, aminoalkyl, aminodialkyl, or halogen;
R$_5$ is each independently substituted alkyl, unsubstituted alkyl, substituted alkenyl, unsubstituted alkenyl, substituted alkynyl, unsubstituted alkynyl, or halogen;
R$_6$ is substituted C$_{1-10}$alkyl or unsubstituted C$_{1-10}$alkyl;
R$_7$ is H or a group selected from any one of groups J, K and H

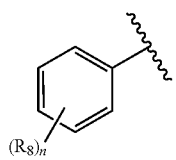
J

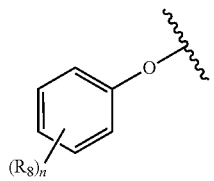
K

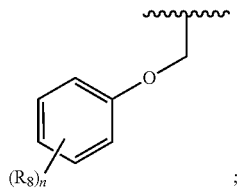
H and
R$_8$ is each independently substituted alkyl, unsubstituted alkyl, substituted O-alkyl, unsubstituted O-alkyl or halogen;
n for R$_4$ and when R$_1$ is not N, is 0, 1, 2, 3 or 4;
n for R$_4$ and when R$_1$ is N, is 0, 1, 2 or 3;
n for R$_5$ is 0, 1, 2, 3, 4 or 5; and
n for R$_8$ is 0, 1, 2, 3, 4 or 5.

17. A compound according to Formula I or Formula II:

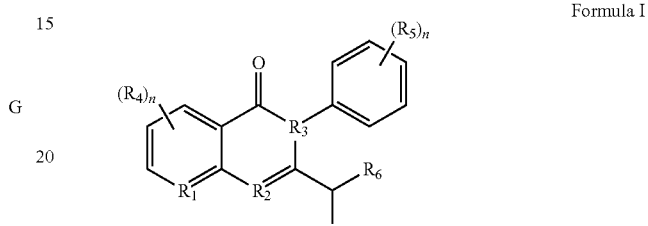
Formula I

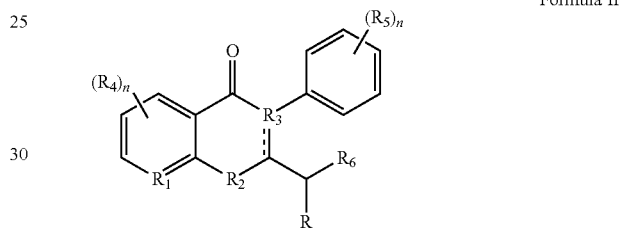
Formula II or a pharmaceutically acceptable salt thereof, wherein
R is H or any one of groups A-G:

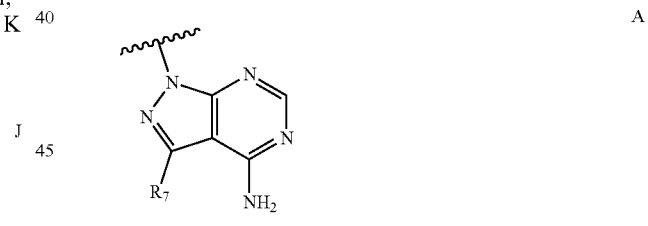
A

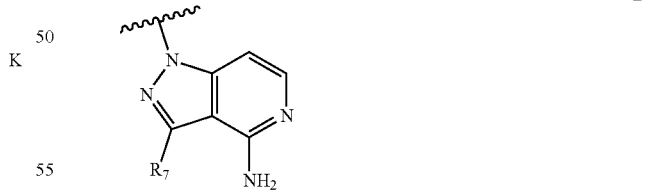
B

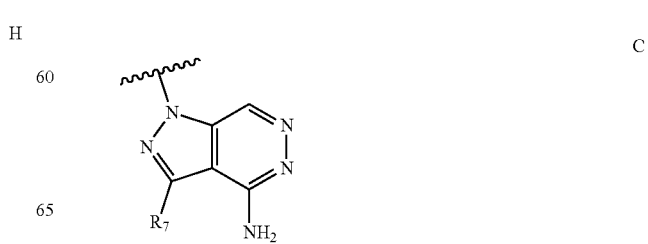
C

-continued

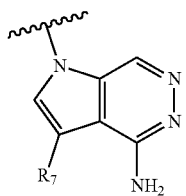
D

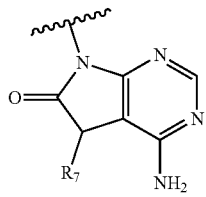
E

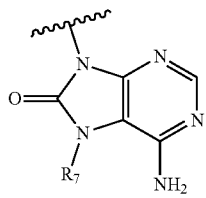
F

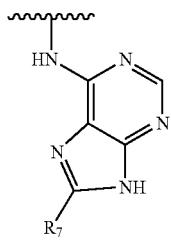
G and wherein
═ represents a single or double bond;
$R_1$ is N;
$R_2$
in the compound of Formula I is CH, substituted C or N;
in the compound of Formula II is O, $CH_2$, substituted C, NH or substituted N;
$R_3$
in the compound of Formula I is CH, substituted C or N;

in the compound of Formula II is
CH, substituted C or N when ═ represents a single bond; or
C when ═ represents a double bond;
$R_4$ is each independently aminoalkyl or aminodialkyl, and optionally halogen;
$R_5$ is each independently substituted alkyl, unsubstituted alkyl, substituted alkenyl, unsubstituted alkenyl, substituted alkynyl, unsubstituted alkynyl, or halogen;
$R_6$ is substituted $C_{1-10}$alkyl or unsubstituted $C_{1-10}$alkyl;
$R_7$ is H or a group selected from any one of groups J, K and H

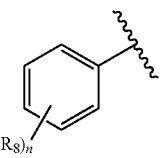
J

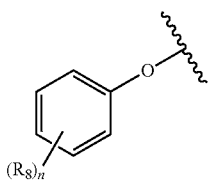
K

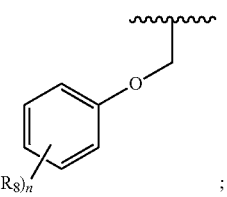
H and
$R_8$ is each independently substituted alkyl, unsubstituted alkyl, substituted O-alkyl, unsubstituted O-alkyl or halogen;
n for $R_4$ and when $R_1$ is not N, is 0, 1, 2, 3 or 4;
n for $R_4$ and when $R_1$ is N, is 0, 1, 2 or 3;
n for $R_5$ is 0, 1, 2, 3, 4 or 5; and
n for $R_8$ is 0, 1, 2, 3, 4 or 5.

18. The compound of claim 17, wherein the aminodialkyl of R4 is —$N(CH_3)_2$.

19. The compound of claim 18, wherein n for $R_4$ is 2 and R4 is —$N(CH_3)_2$ and bromide.

* * * * *